United States Patent
Fujii et al.

(10) Patent No.: US 10,416,160 B2
(45) Date of Patent: Sep. 17, 2019

(54) MEMORY INVARIANT NKT CELL MARKER

(71) Applicant: RIKEN, Wako-shi, Saitama (JP)

(72) Inventors: Shin-ichiro Fujii, Wako (JP); Kanako Shimizu, Wako (JP); Osamu Ohara, Wako (JP); Takashi Watanabe, Wako (JP)

(73) Assignee: RIKEN, Wako (JP)

( * ) Notice: Subject to any disclaimer, the term of this patent is extended or adjusted under 35 U.S.C. 154(b) by 0 days.

(21) Appl. No.: 15/328,997

(22) PCT Filed: Jul. 24, 2015

(86) PCT No.: PCT/JP2015/071157
§ 371 (c)(1),
(2) Date: Jan. 25, 2017

(87) PCT Pub. No.: WO2016/013672
PCT Pub. Date: Jan. 28, 2016

(65) Prior Publication Data
US 2017/0227540 A1 Aug. 10, 2017

(30) Foreign Application Priority Data
Jul. 25, 2014 (JP) .................. 2014-152394

(51) Int. Cl.
*G01N 33/569* (2006.01)
*G01N 33/53* (2006.01)
*C07K 16/28* (2006.01)
*C12Q 1/04* (2006.01)
*C12Q 1/24* (2006.01)

(52) U.S. Cl.
CPC ......... *G01N 33/56972* (2013.01); *C12Q 1/04* (2013.01); *C12Q 1/24* (2013.01); *G01N 33/53* (2013.01); *C07K 16/28* (2013.01); *G01N 2800/52* (2013.01)

(58) Field of Classification Search
CPC .... G01N 33/56972; G01N 33/53; C12Q 1/04; C12Q 1/24; C07K 16/28
See application file for complete search history.

(56) References Cited

U.S. PATENT DOCUMENTS

| 2010/0086550 A1 | 4/2010 | Kang et al. |
| 2011/0004953 A1 | 1/2011 | Watanabe et al. |
| 2013/0136735 A1 | 5/2013 | Truneh et al. |

FOREIGN PATENT DOCUMENTS

| JP | 2010-083863 A | 4/2010 |
| JP | 2013-034459 A | 2/2013 |
| WO | 2013/063395 A | 5/2013 |

OTHER PUBLICATIONS

Arrunategui-Correa et al., *Gastroenterology*, 126(4): A294, abstract M1085 (2004).
Berzins et al., *Nat. Rev. Immunol.*, 11(2): 131-142 (2011).
Beyersdorf et al., *Eur. J. Immunol.*, 31(12): 3443-3452 (2001).
Bezman et al., *Nat. Immunol.*, 13(10): 1000-1009 (2012).
Cerundolo et al., *Nat. Rev. Immunol.*, 9(1): 28-38 (2009).
Chang et al., *J. Exp. Med.*, 201(9): 1503-1517 (2005).
Cooper et al., *Proc. Natl. Acad. Sci. USA*, 106(6): 1915-1919 (2009).
Fujii et al., *Blood*, 113(18): 4262-4272 (2009).
Fujii et al., *Nat. Immunol.*, 3(9): 867-874 (2002).
Fujii et al., *Semin. Immunol.*, 22(2): 97-102 (2010).
Godfrey et al., *Nat. Immunol.*, 11(3): 197-206 (2010).
Konsta et al., *Clin. Chem. Lab. Med.*, 48(9): A169 (2010).
Malaisé et al., *J. Immunol.*, 192(4): 1954-1961 (2014).
Matsumoto et al., "NK Saibo no Saibo Ninshiki Kiko to Shikkan Hi MHC Class I Bunshi o Ligand to suru NK Saibo Yokuseisei Receptor KLRG1 to LAIR-1," *Experimental Medicine*, 25(9): 1293-1300 (2007).
Min-Oo et al., *Trends Immunol.*, 34(6): 251-258 (2013).
Motohashi et al., *Front. Biosci. (Schol. Ed.)*, S1: 108-116 (2009).
Motohashi et al., *J. Immunol.*, 182(4): 2492-2501 (2009).
Nieda et al., *Blood*, 103(2): 383-389 (2004).
O'Leary et al., *Nat. Immunol.*, 7(5): 507-516 (2006).
Sheridan et al., *Immunity*, 39(1): 184-195 (2013).
Shimizu et al., *J. Immunol.*, 178(5): 2853-2861 (2007).
Shimizu et al., *J. Immunol.*, 190(11): 5609-5619 (2013).
Shimizu et al., *Proc. Natl. Acad. Sci. USA*, 111(34): 12474-12479 (2014).
Sun et al., *Nature*, 457(7229): 557-561 (2009).
Japanese Patent Office, International Search Report in International Patent Application No. PCT/JP2015/071157 (dated Sep. 29, 2015).
Japanese Patent Office, Written Opinion of the International Searching Authority in International Patent Application No. PCT/JP2015/071157 (dated Sep. 29, 2015).
Reilly et al., "Activated iNKT Cells Promote Memory $CD8^+T$ Cell Differentiation during Viral Infection," *PLoS One*, 7(5): e37991 (2012).
Tonbo Biosciences, "Purified Anti-Mouse KLRG1 (2F1)," Technical Data Sheet, Catalog No. 70-5893 (2013) [obtained at: http://tds.tonbobio.com/tds-70-5893.pdf].

*Primary Examiner* — Ruixiang Li
(74) *Attorney, Agent, or Firm* — Leydig, Voit & Mayer, Ltd.

(57) ABSTRACT

The present invention provides use of KLRG1 as a marker specific to memory invariant NKT cells. Using an antibody that specifically recognizes KLRG1, memory invariant NKT cells can be easily detected or isolated.

10 Claims, 25 Drawing Sheets

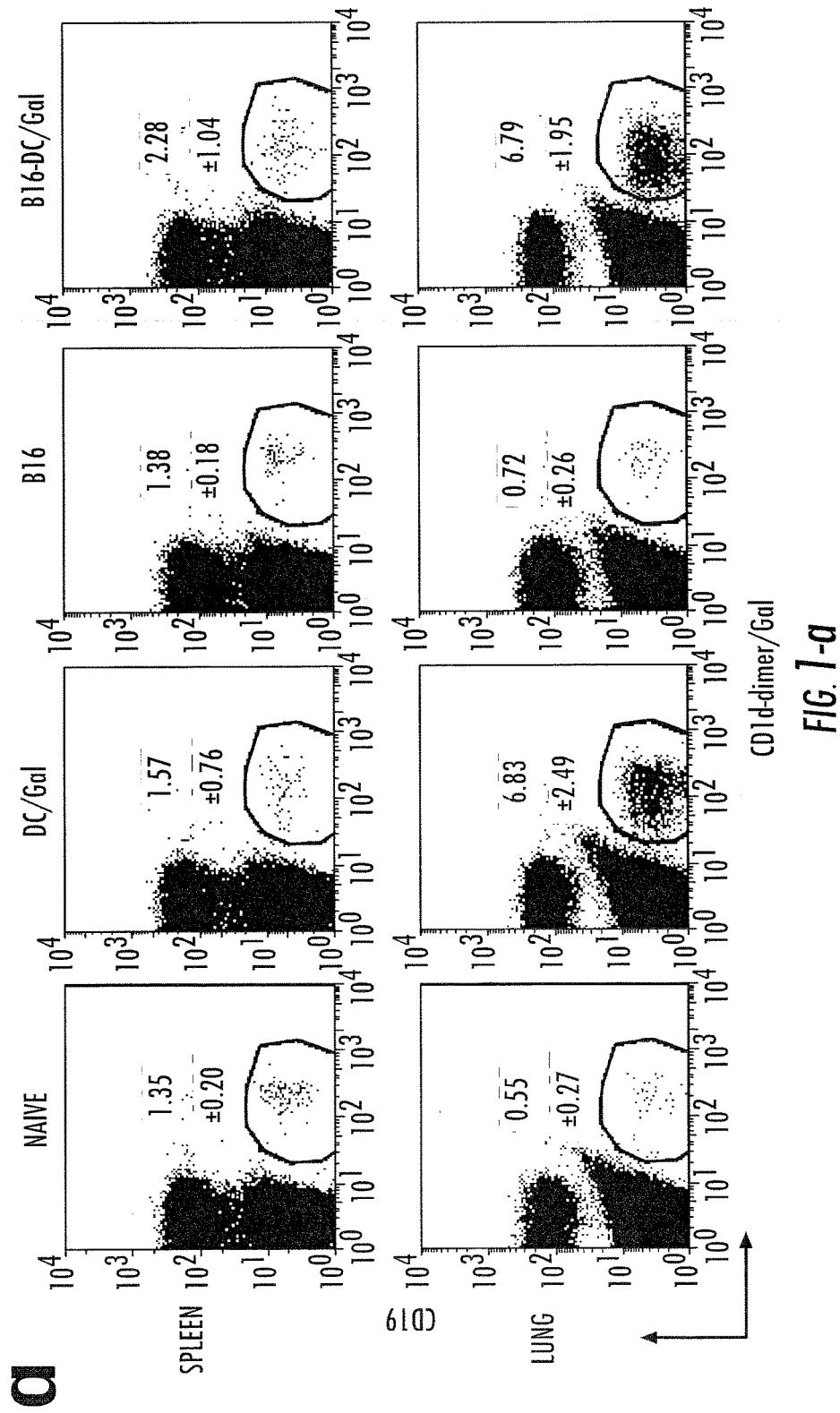
FIG. 1-a

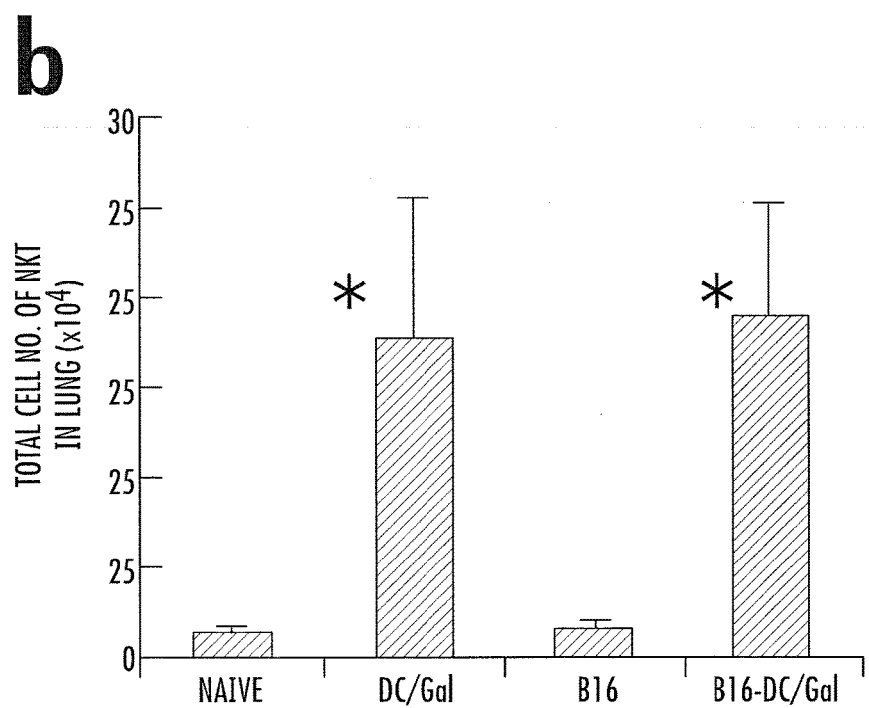
FIG. 1-b

FIG. 1-c
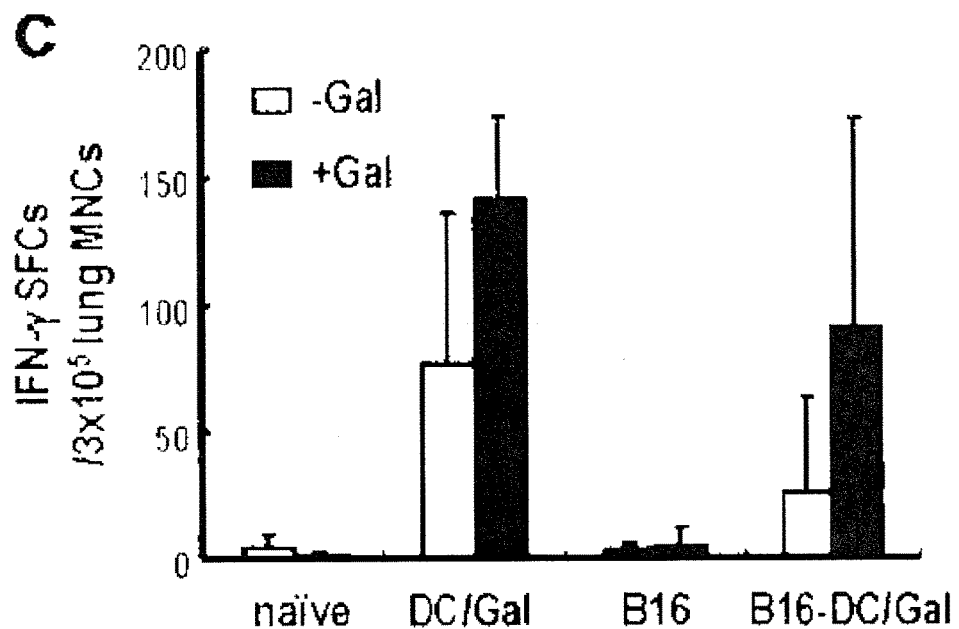
FIG. 1-d
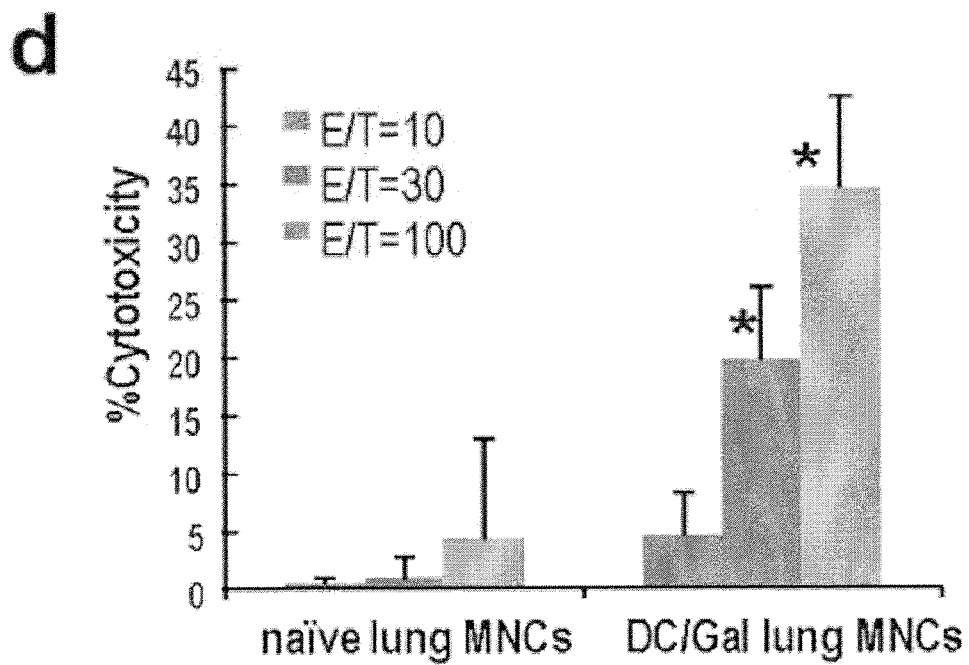

FIG. 1-e
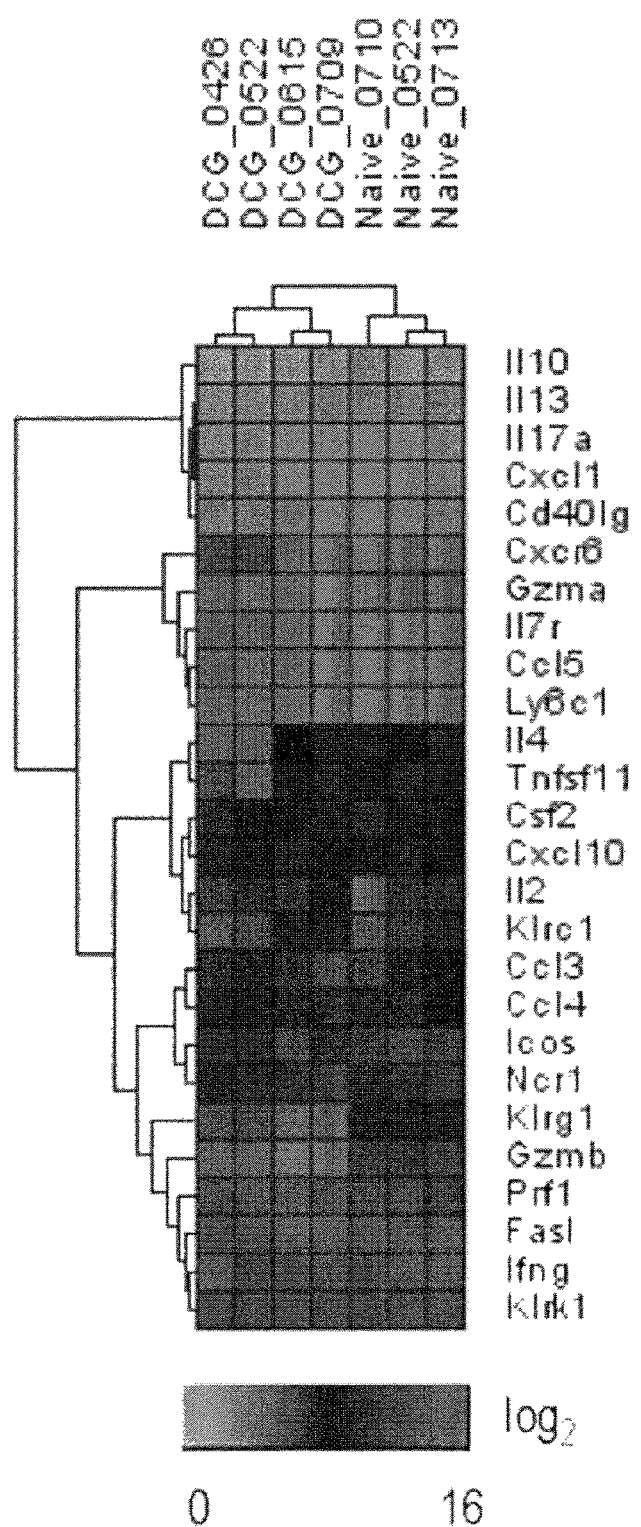

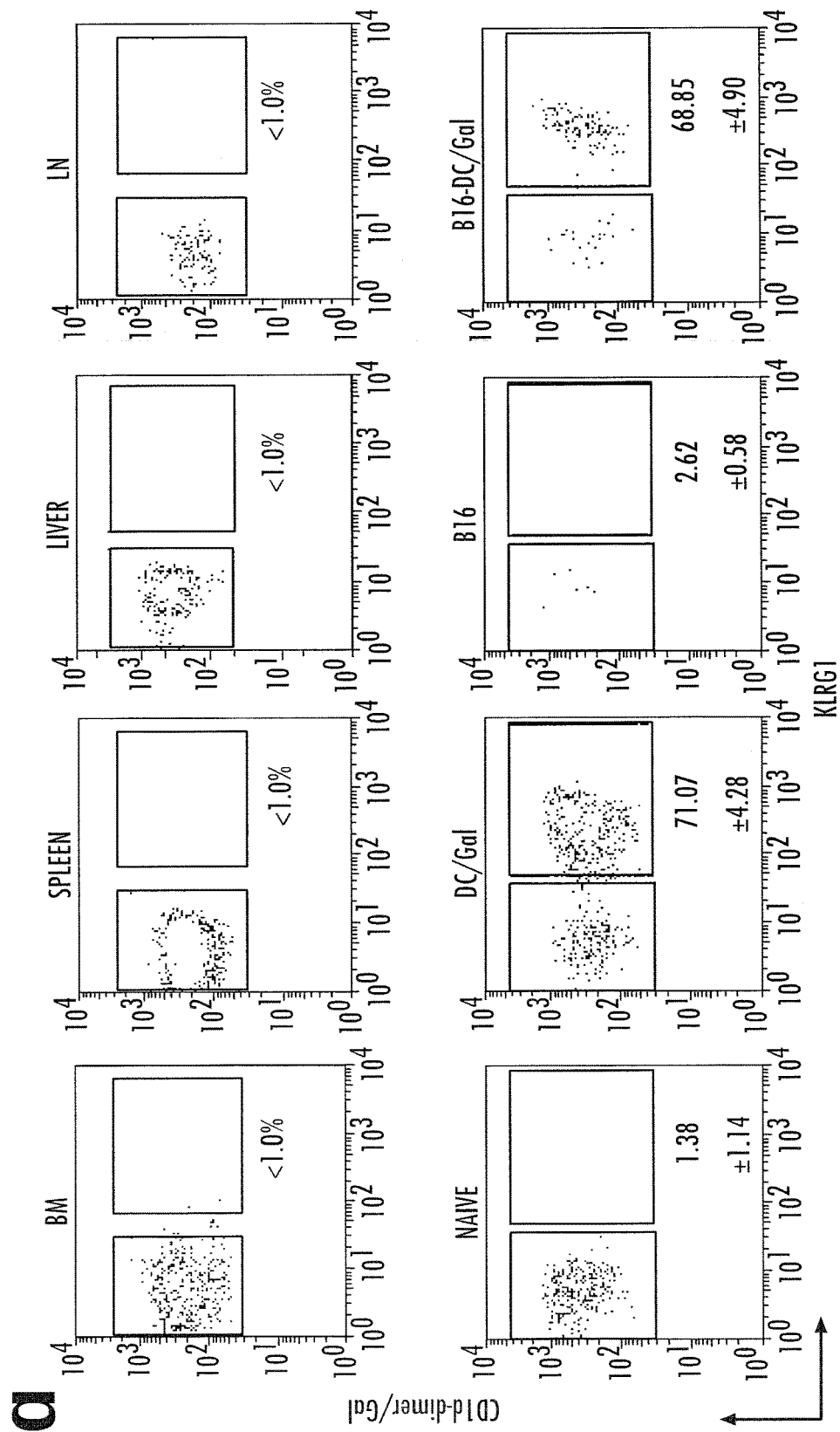
FIG. 2-a

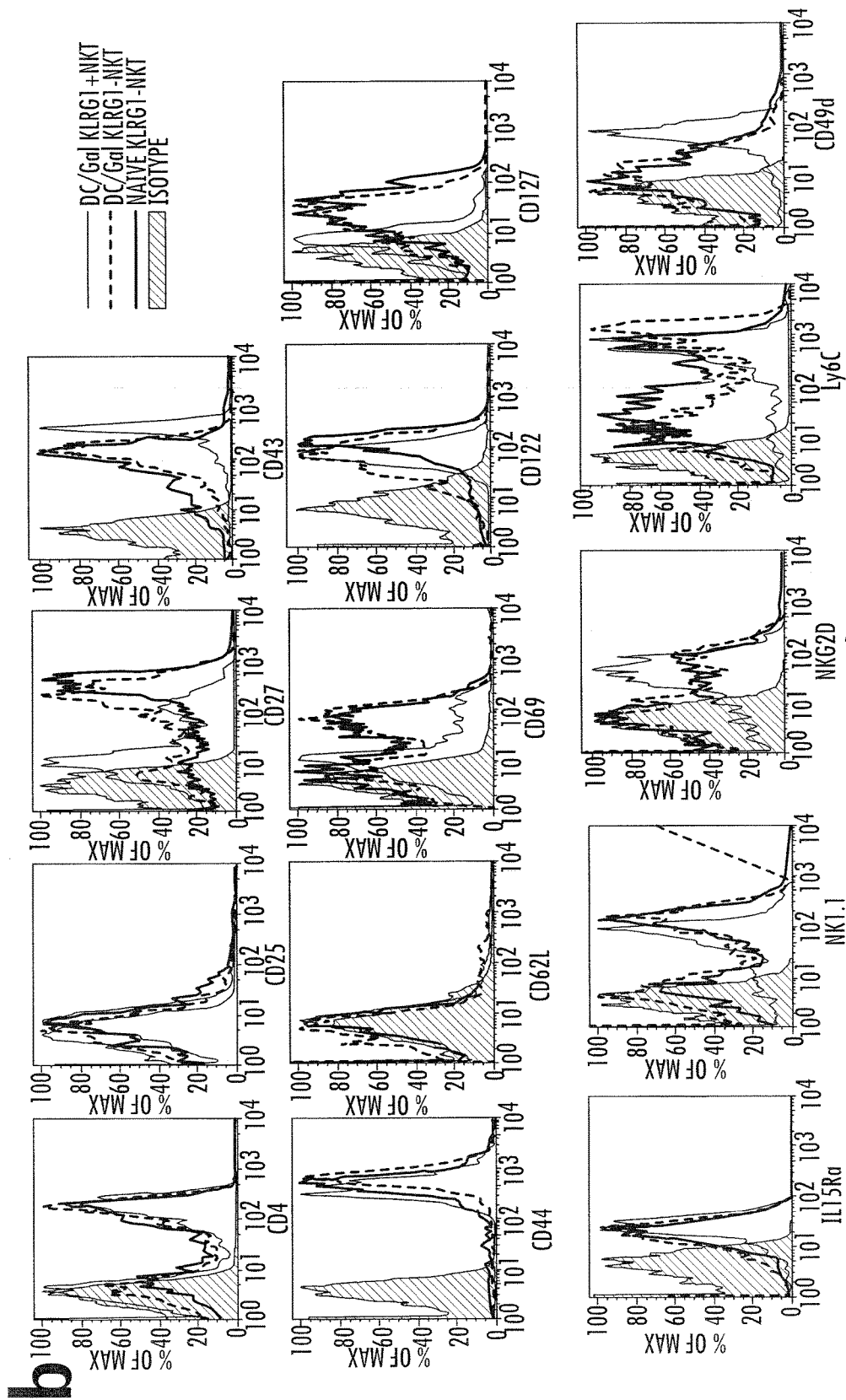
FIG. 2-b

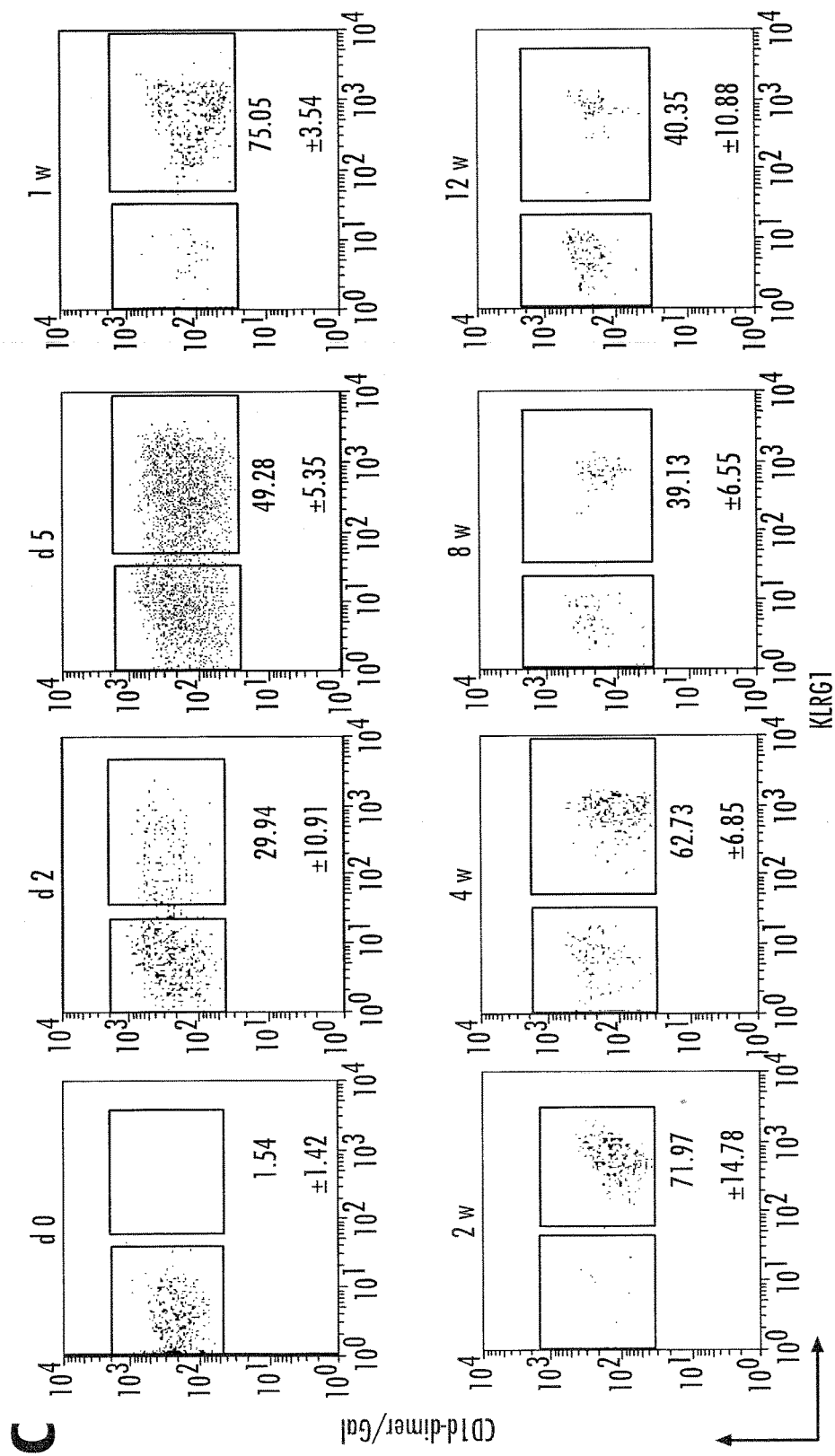
FIG. 2-c

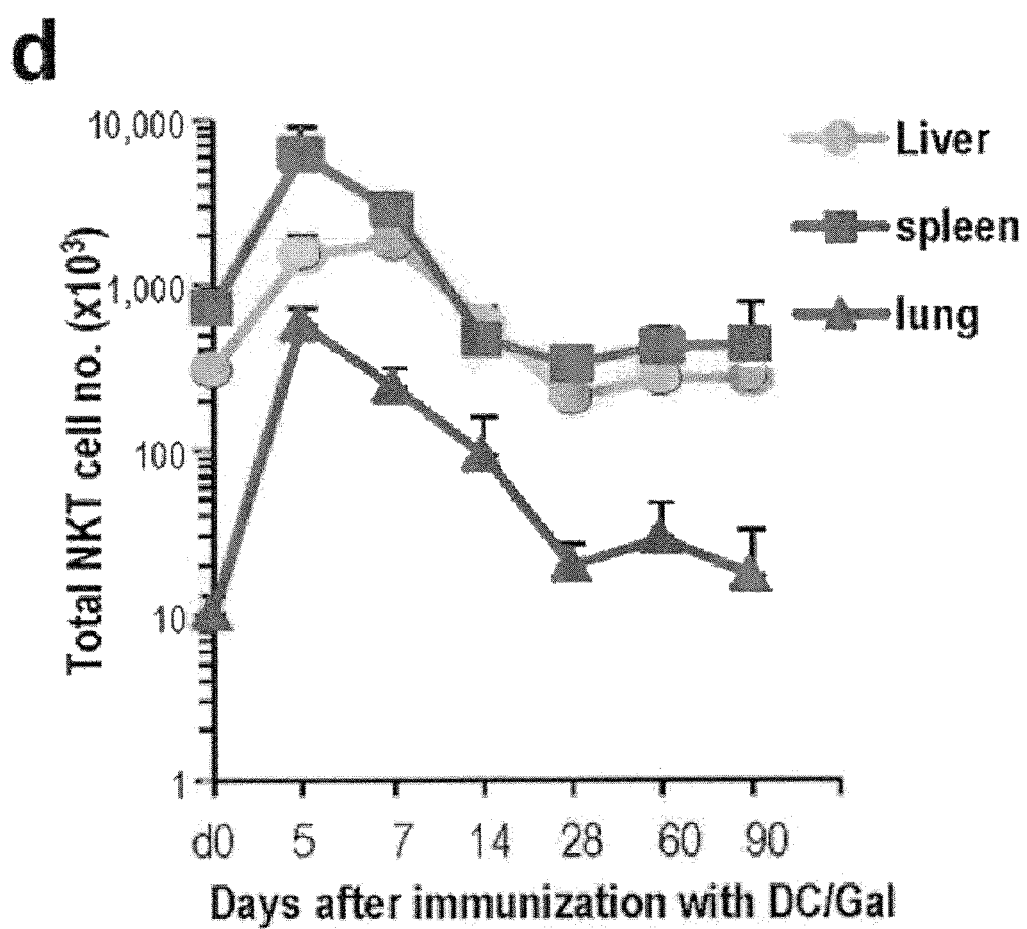
FIG. 2-d

FIG. 2-e
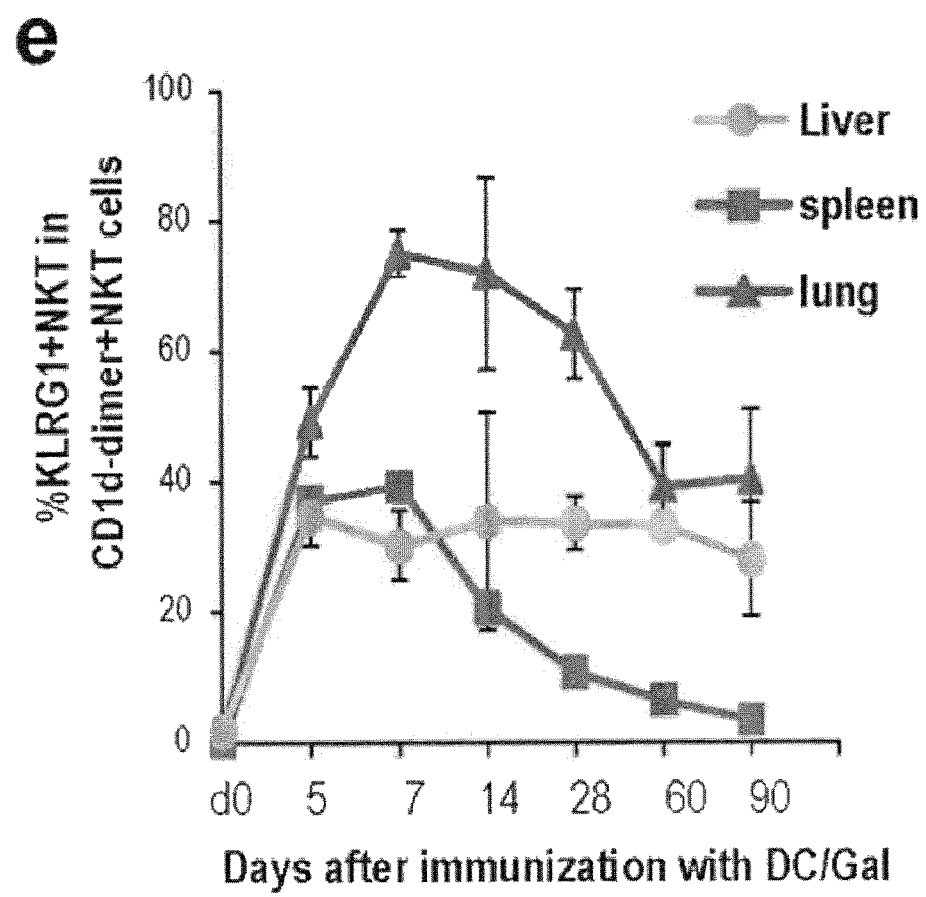

*FIG. 3-a*
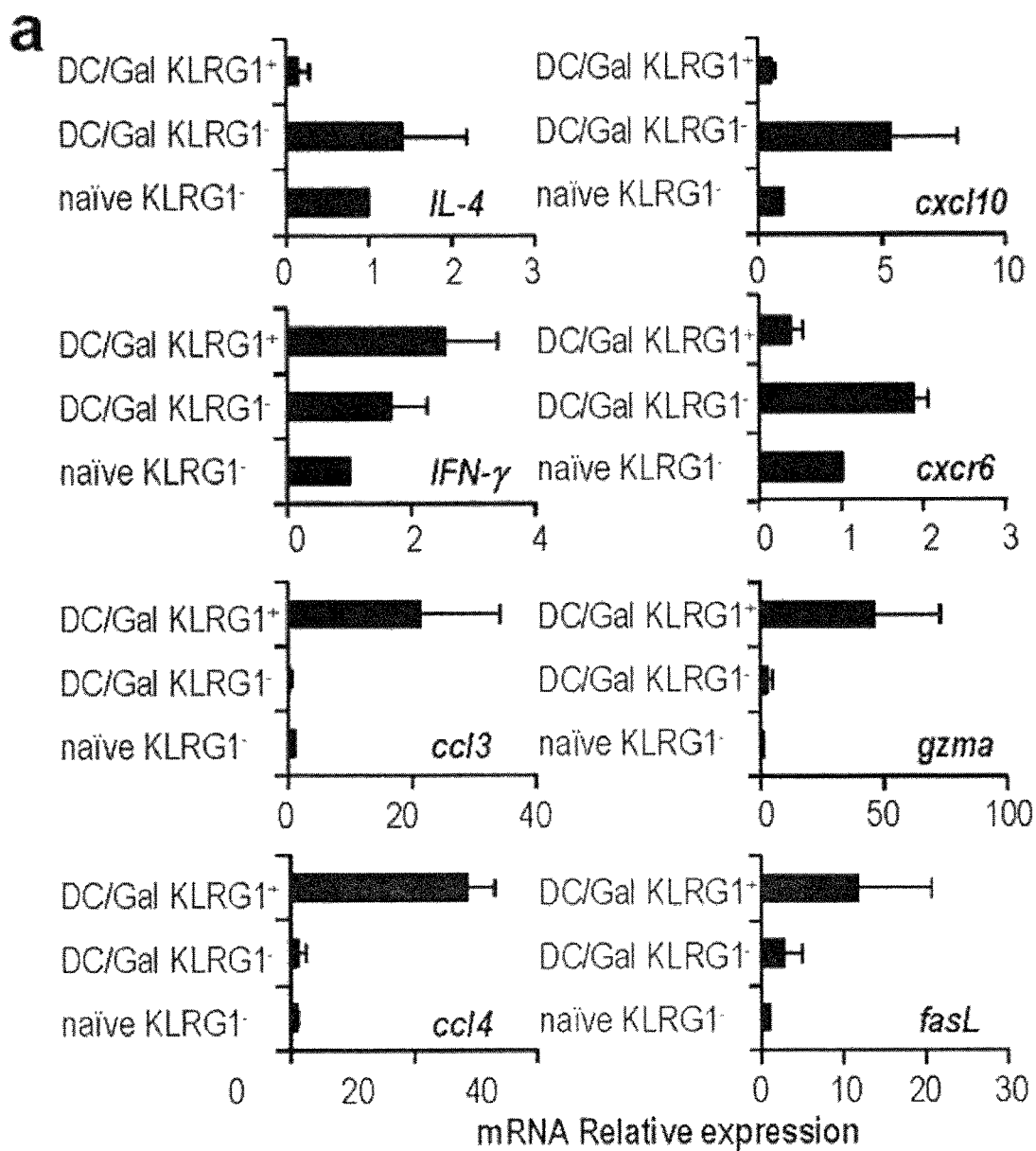

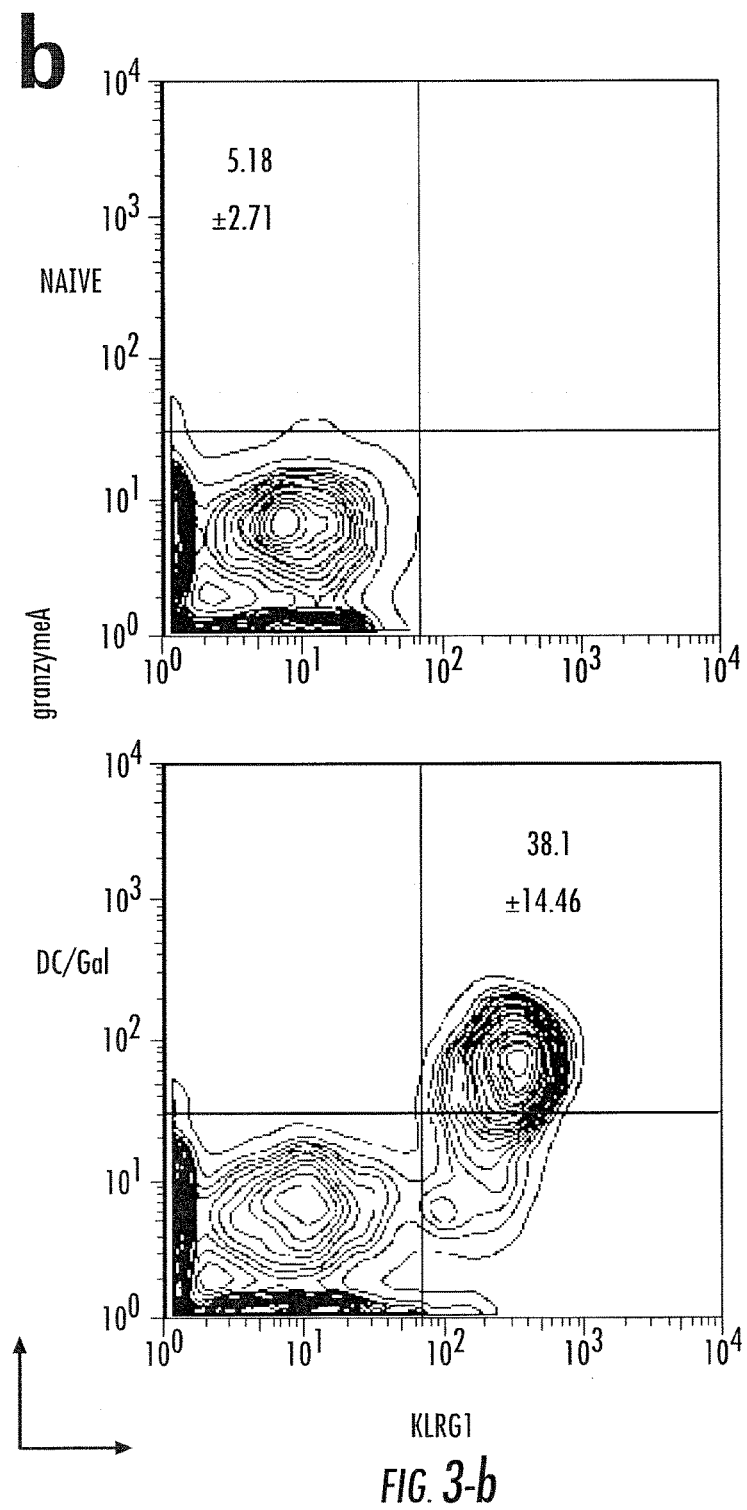
FIG. 3-b

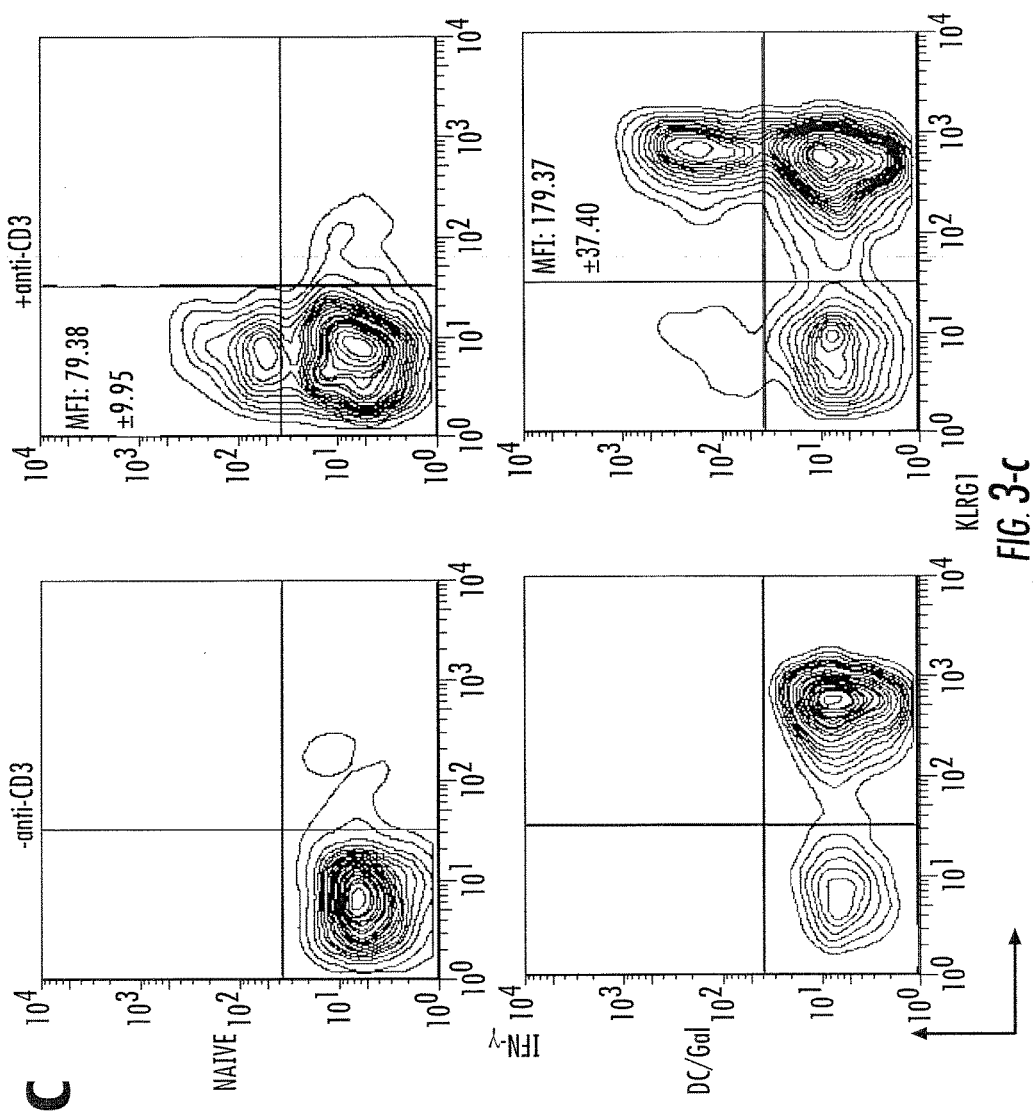
FIG. 3-c

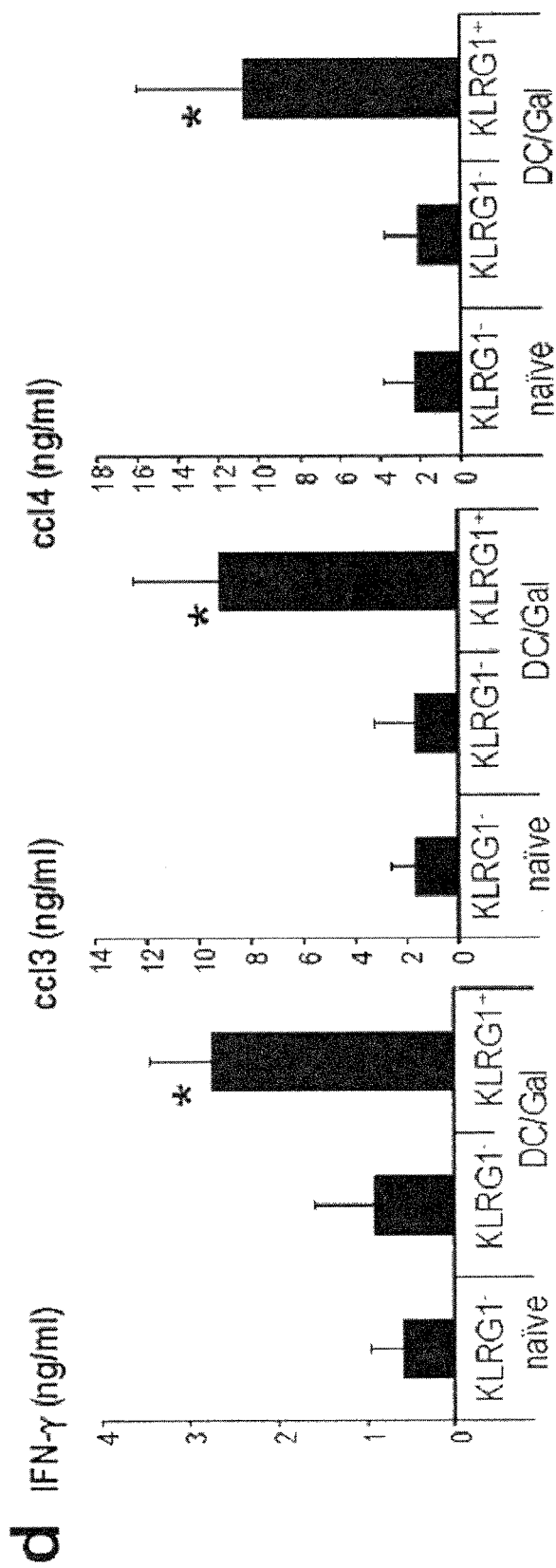
FIG. 3-d

*FIG. 3-e*
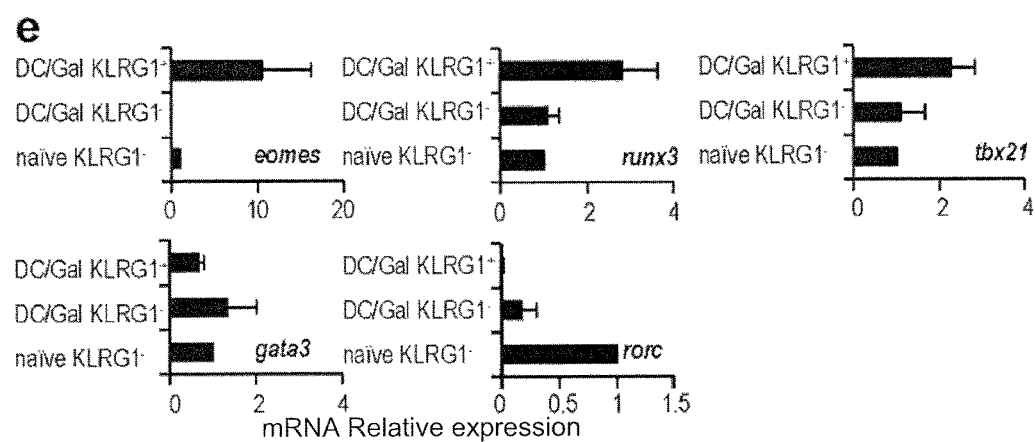

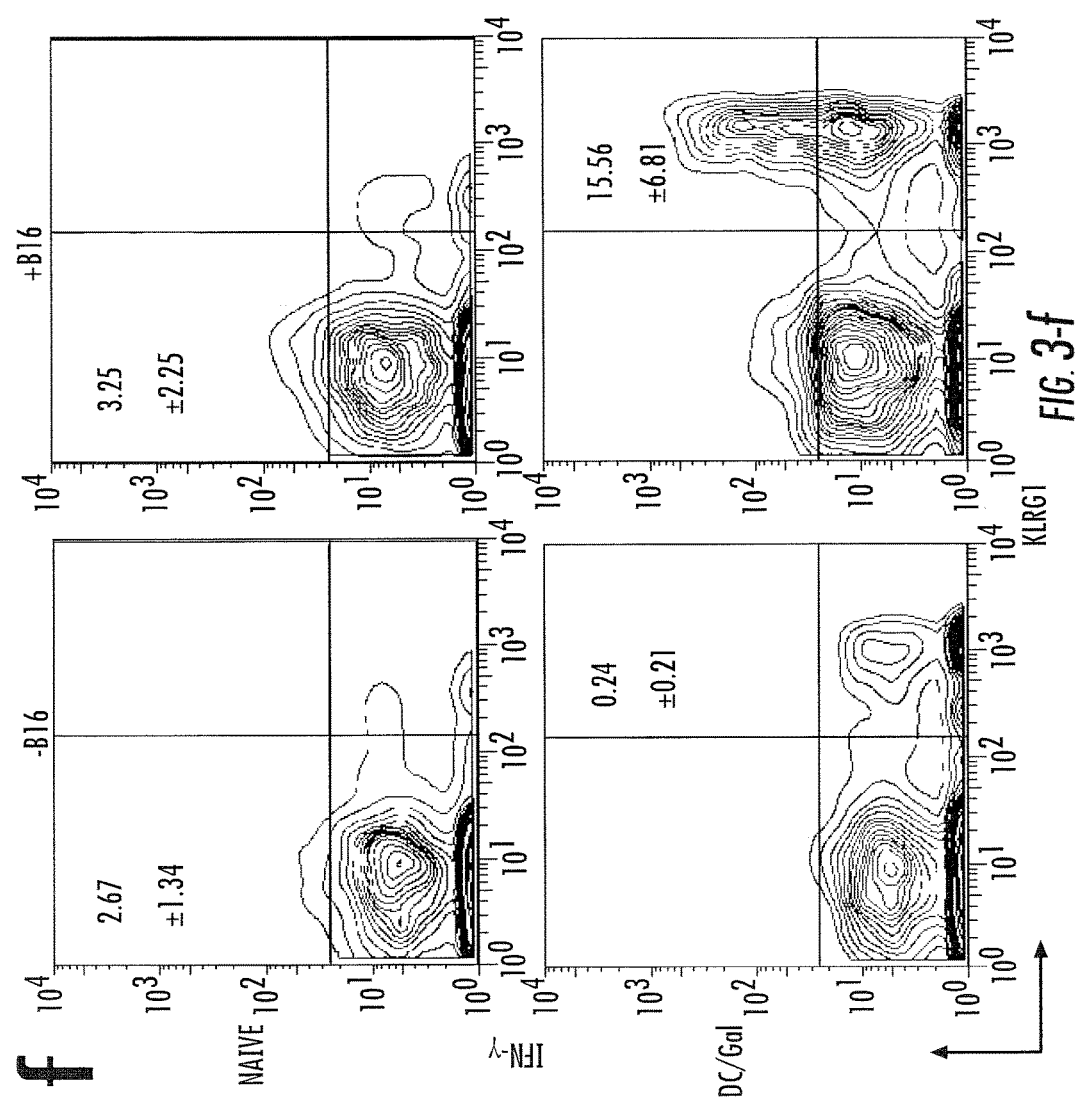
FIG. 3-f

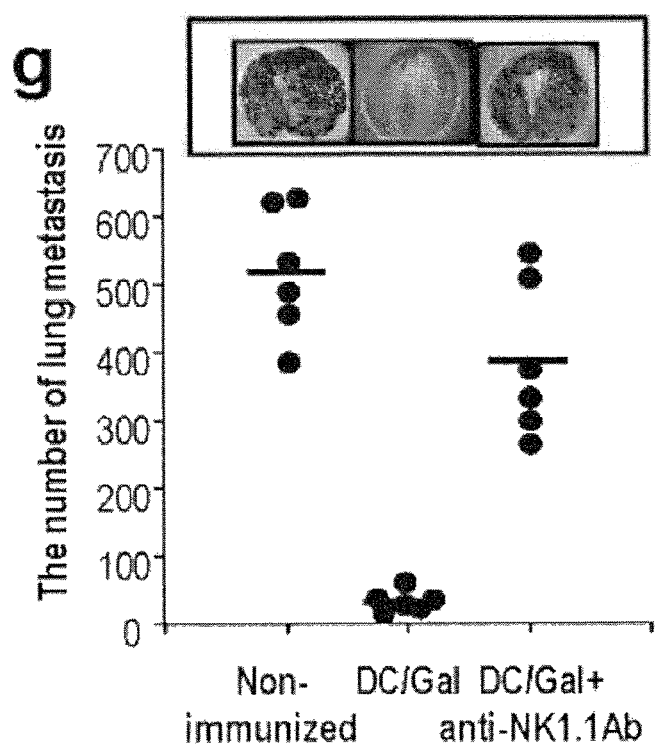
FIG. 3-g

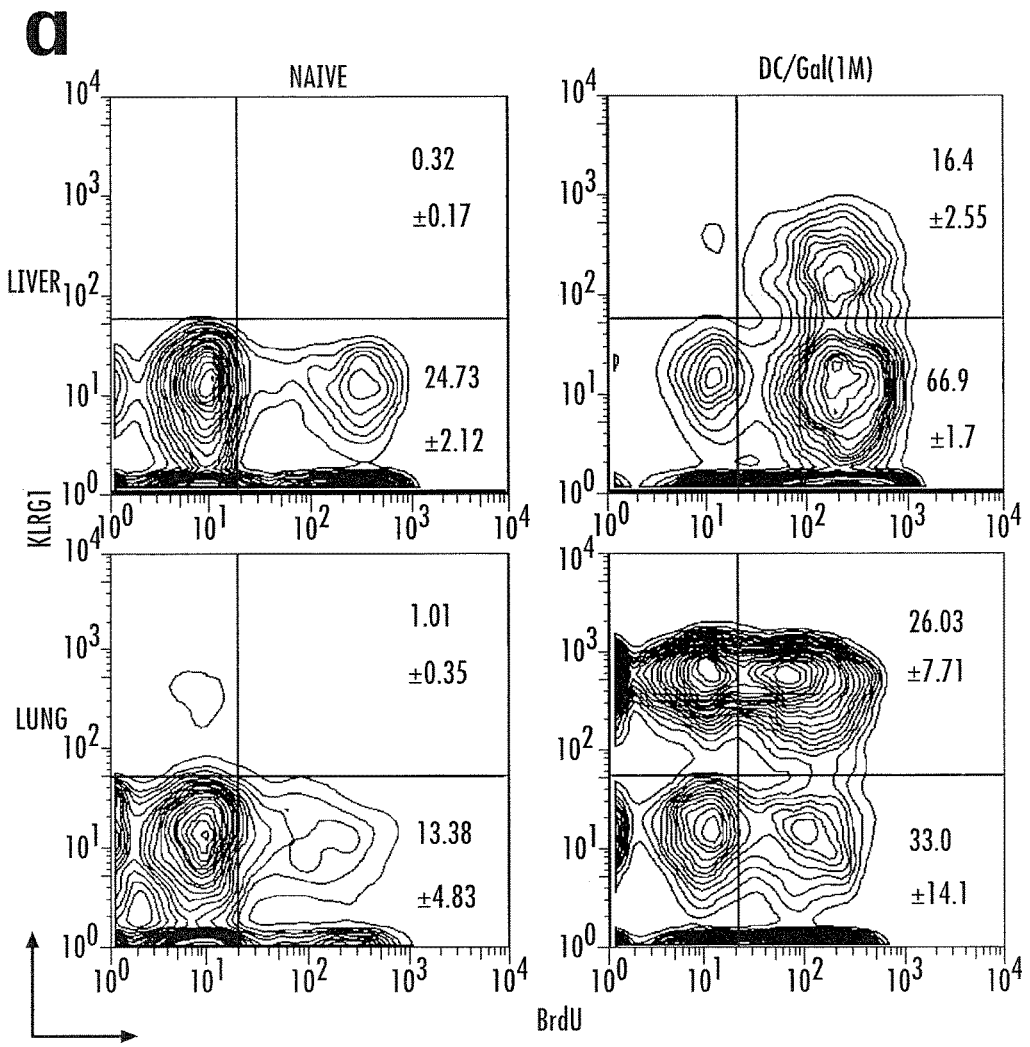
FIG. 4-a

FIG. 4-b
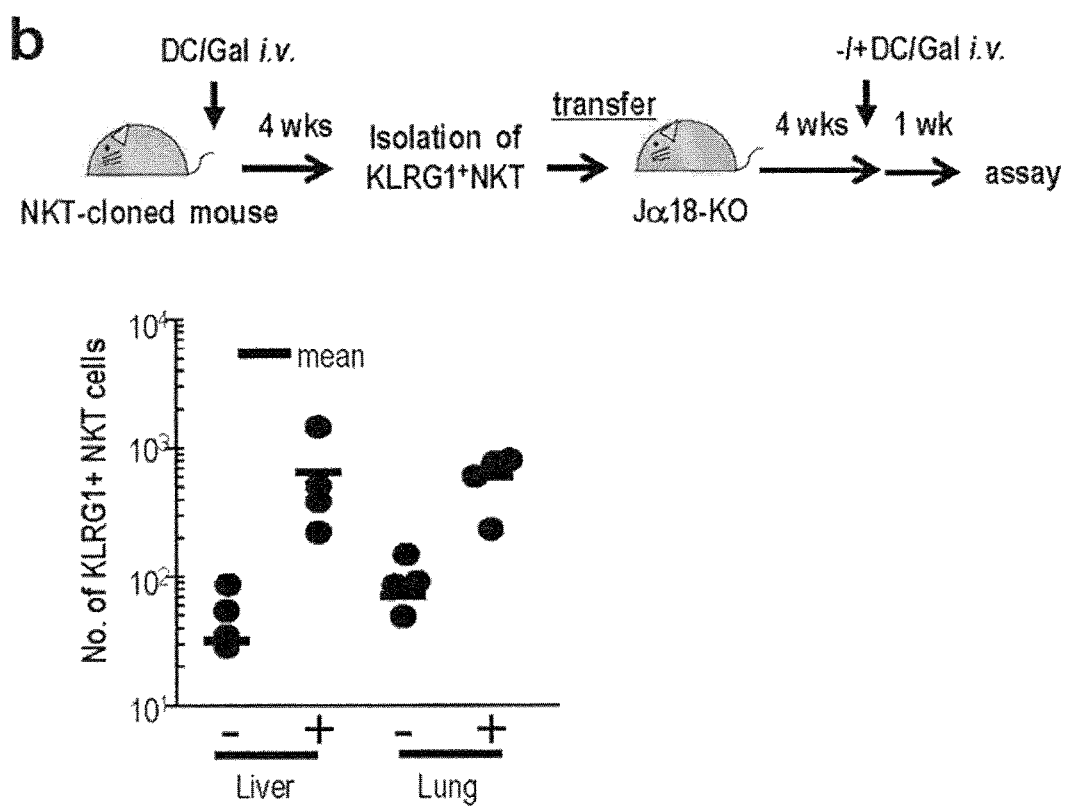

FIG. 4-c
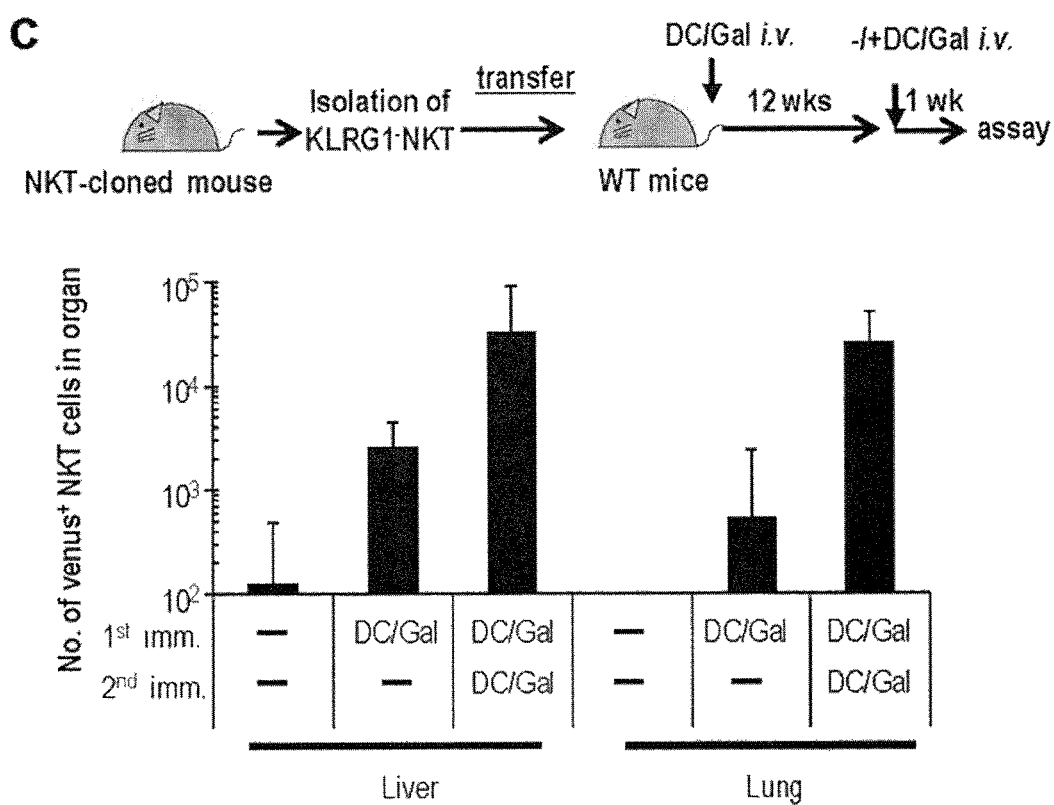

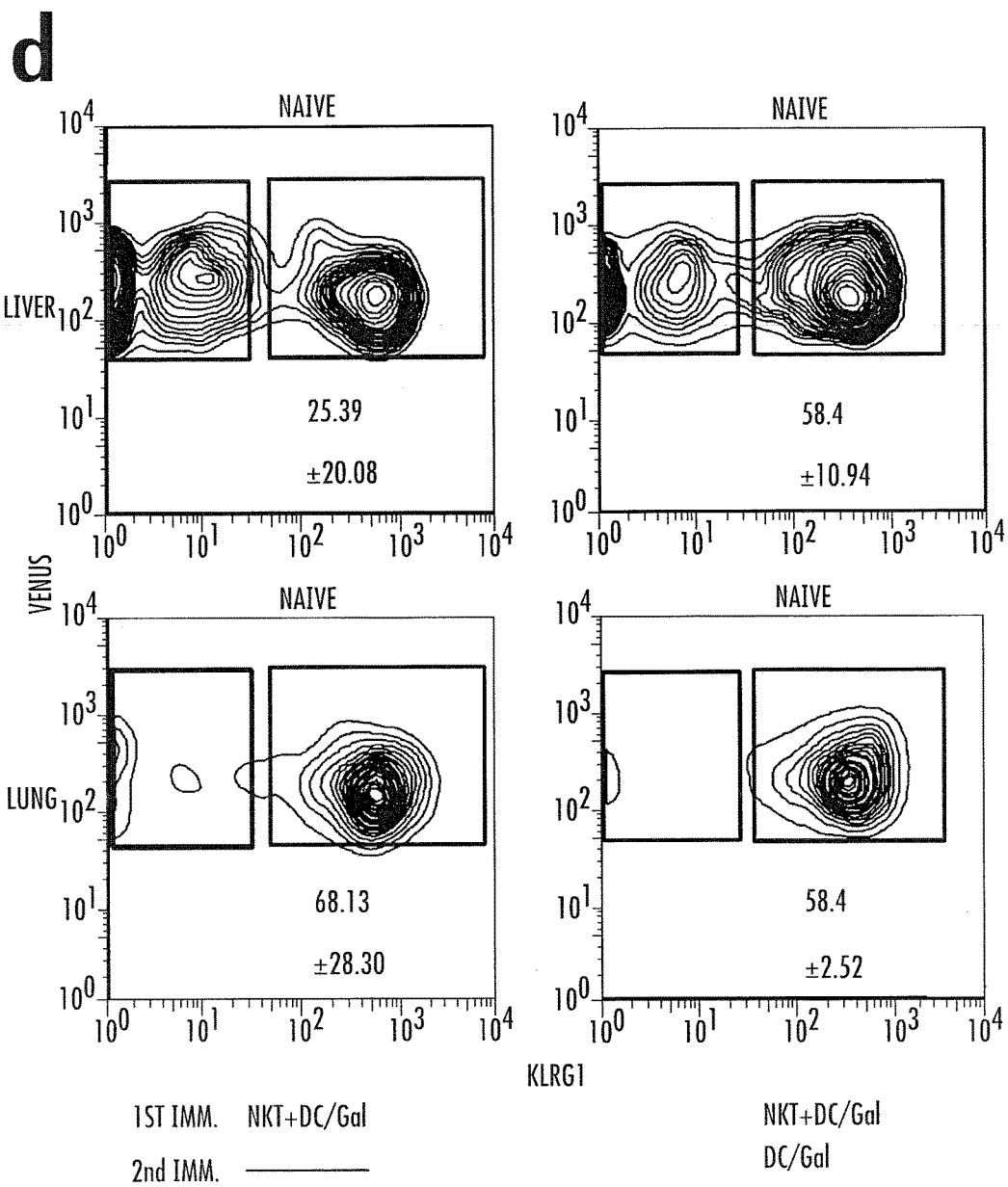
FIG. 4-d

FIG. 4-e
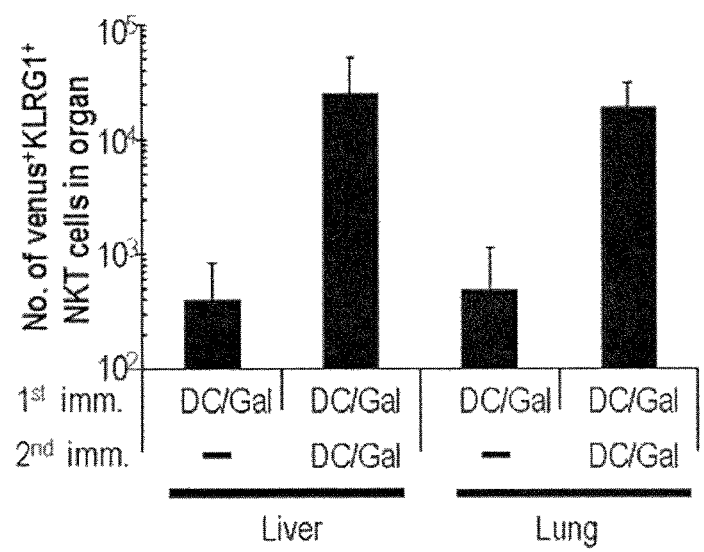
FIG. 5-a
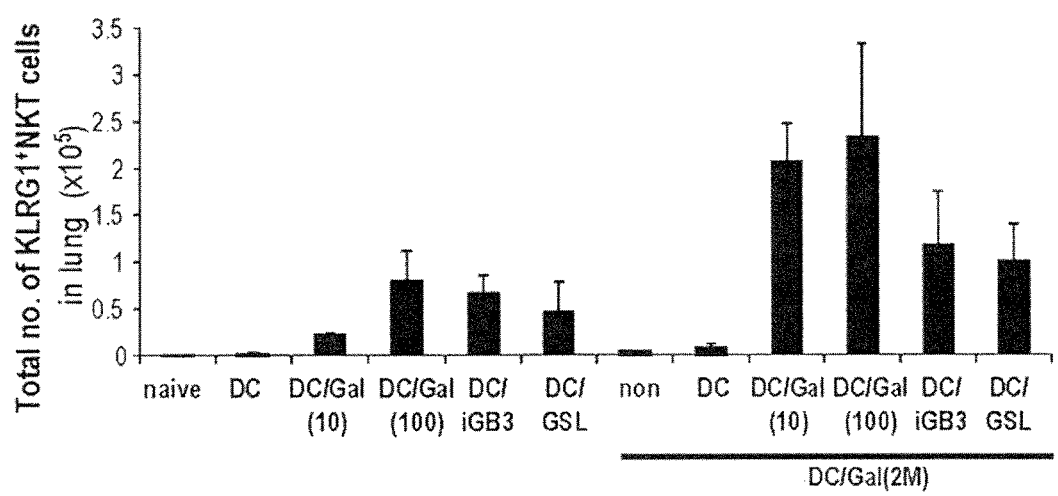

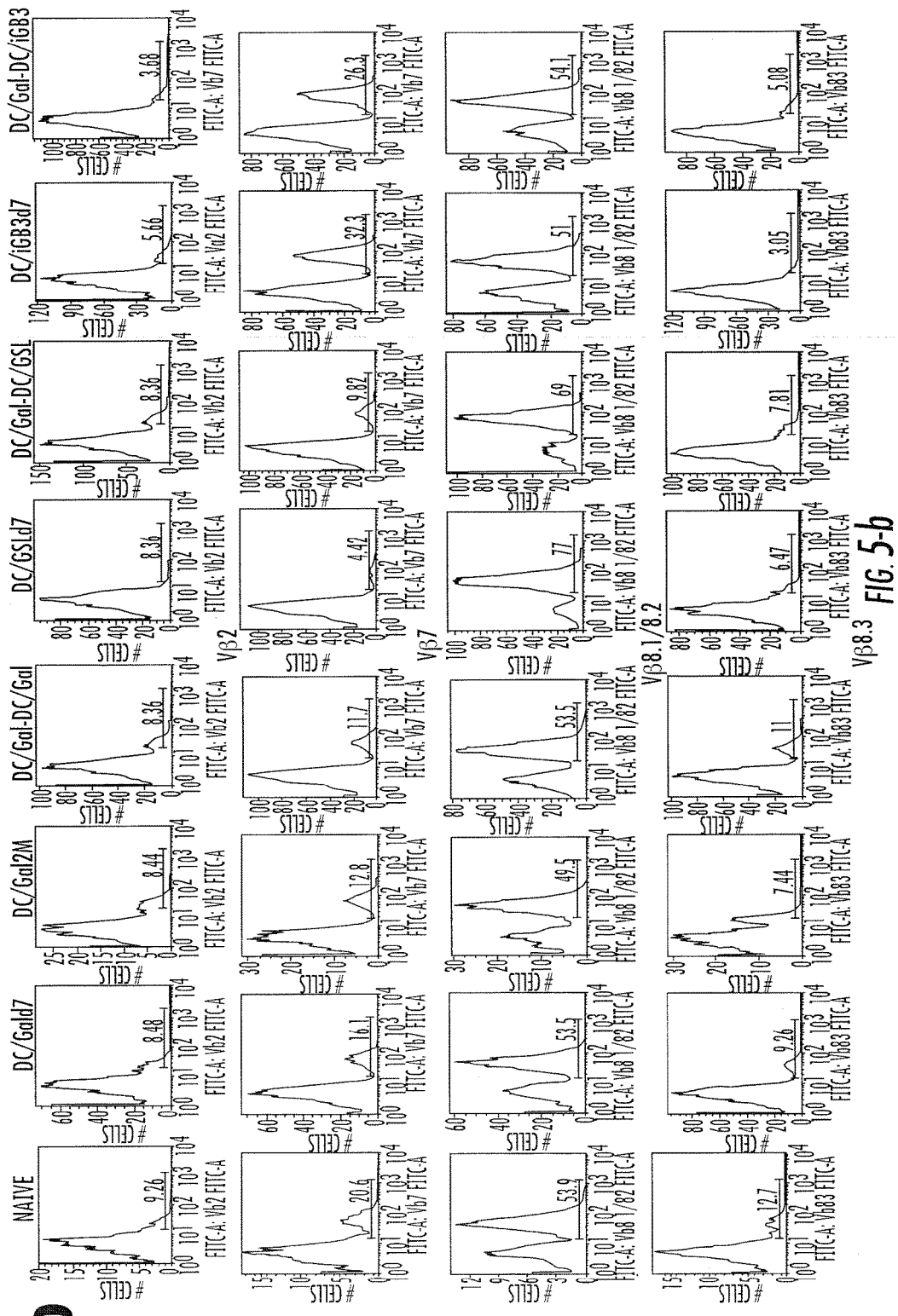
FIG. 5-b

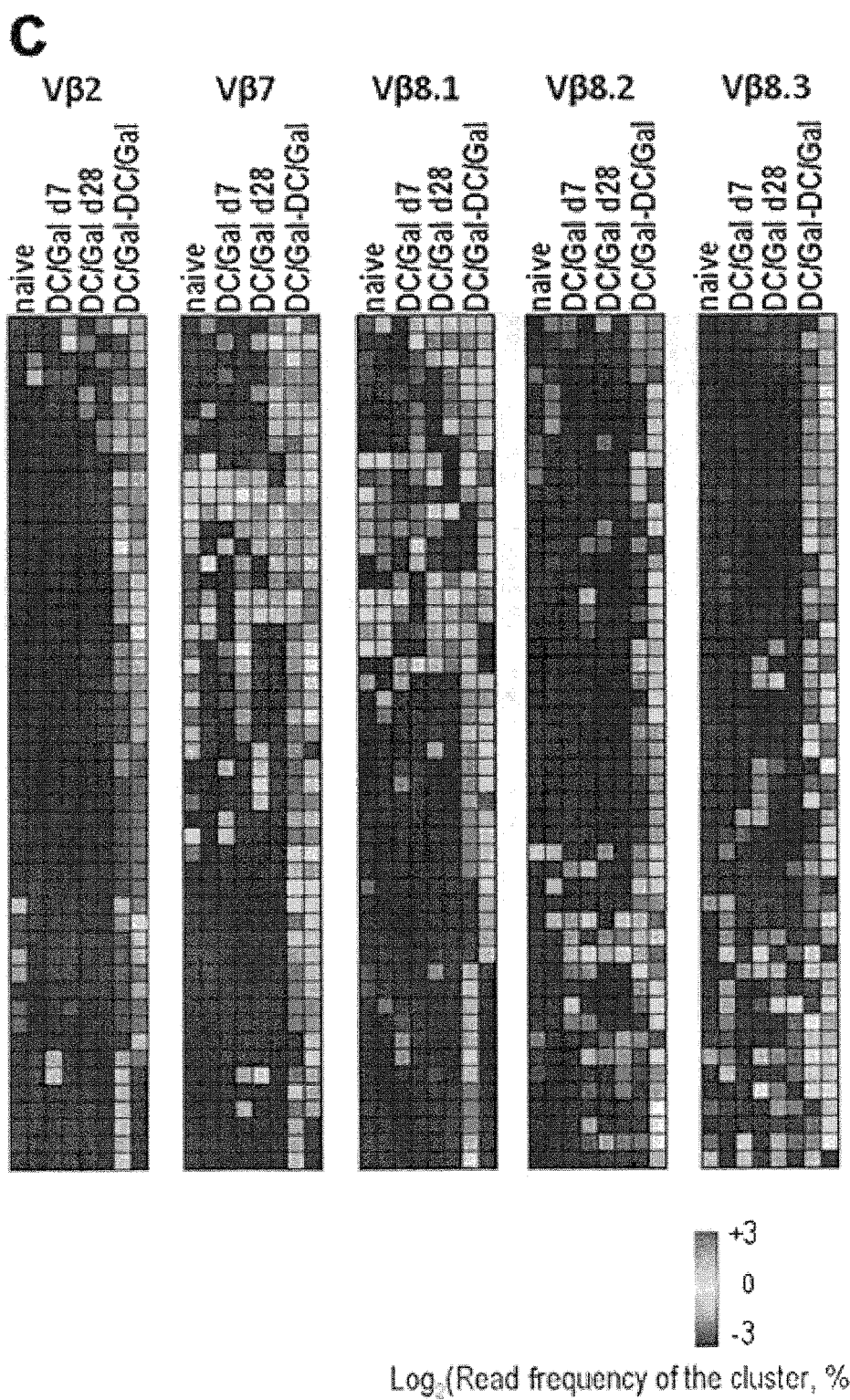
FIG. 5-c

FIG. 5-d
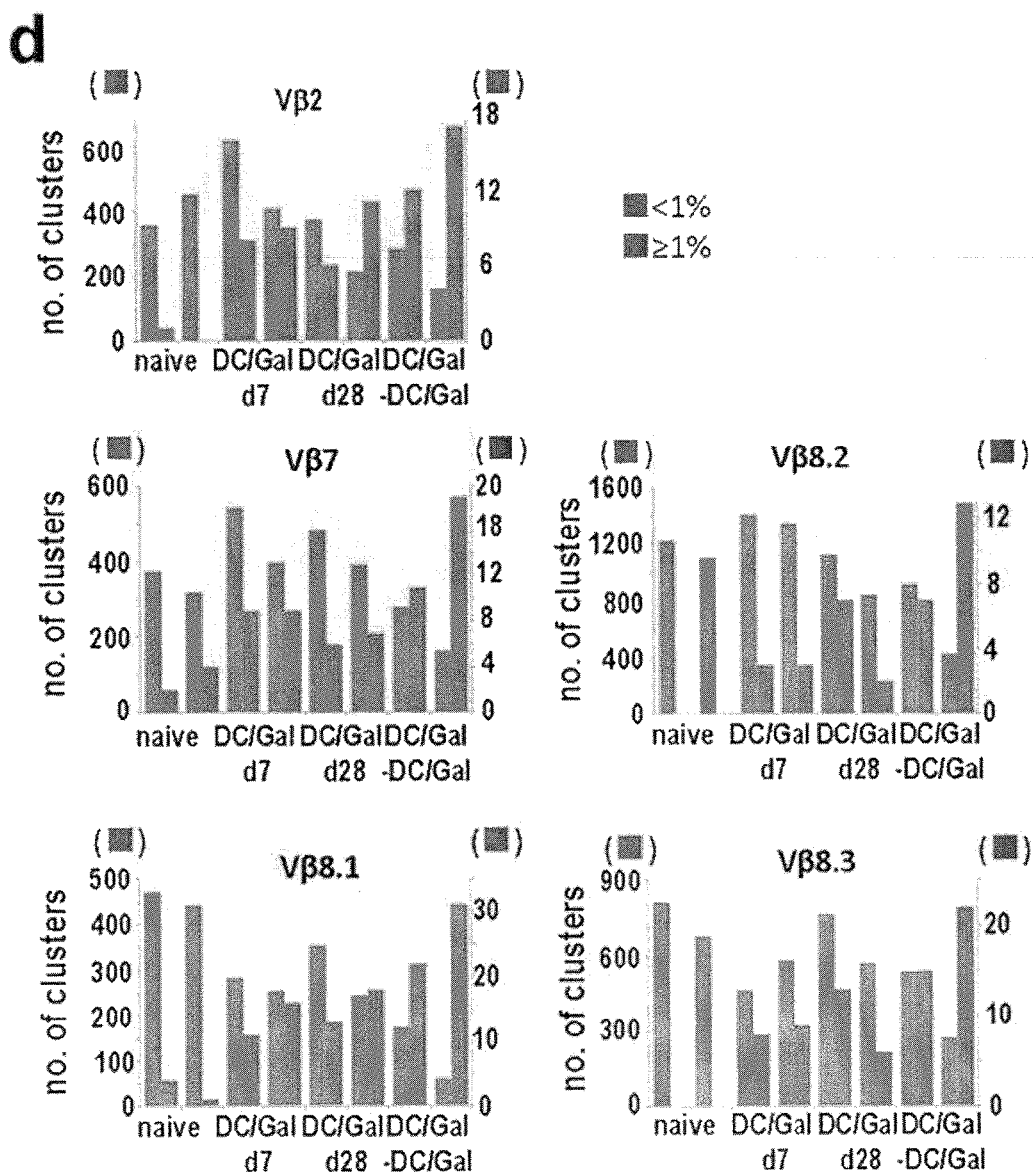

FIG. 5-e
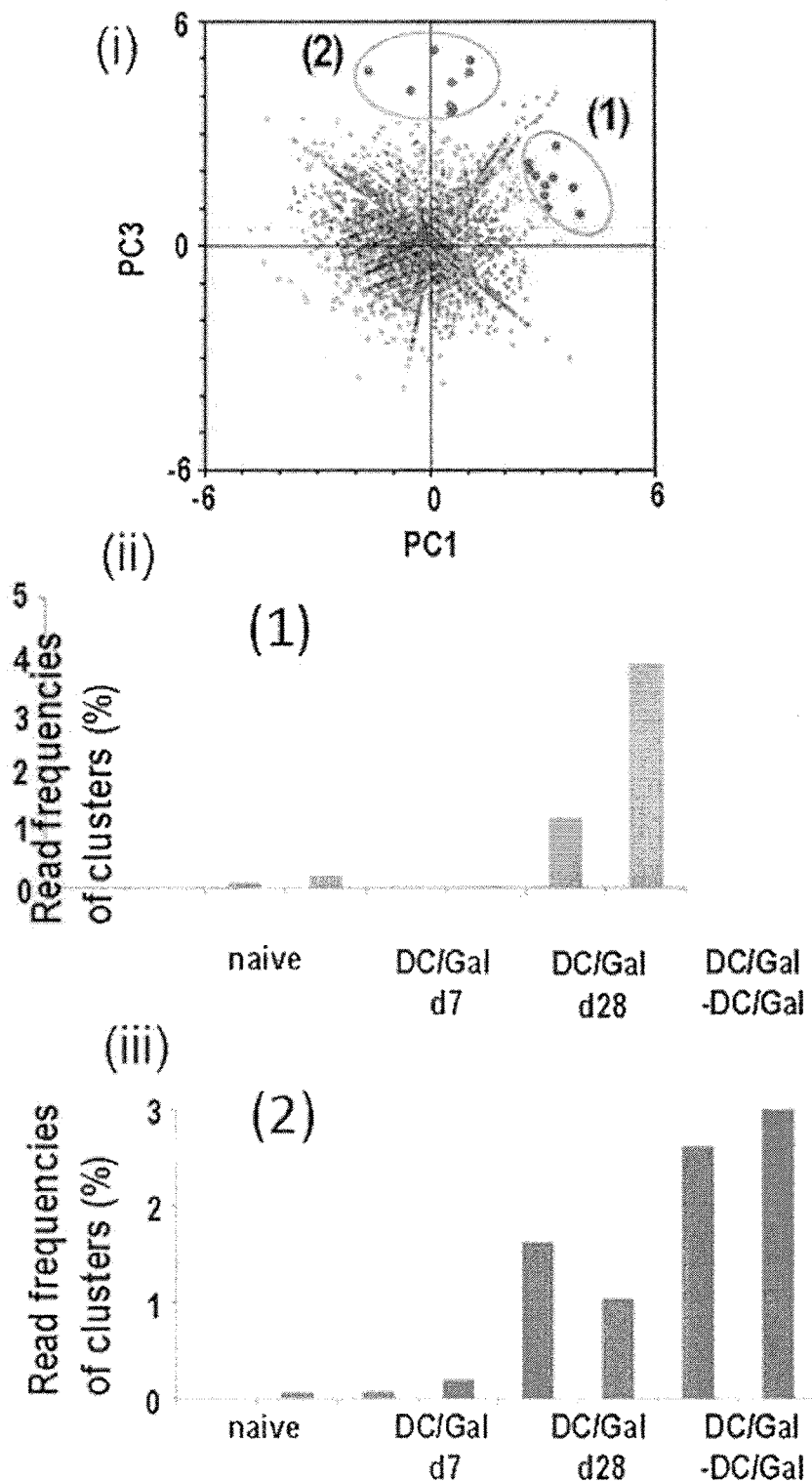

MEMORY INVARIANT NKT CELL MARKER

CROSS-REFERENCE TO RELATED APPLICATIONS

This patent application is the U.S. national phase of International Patent Application No. PCT/JP2015/071157, filed on Jul. 24, 2015, which claims the benefit of Japanese Patent Application No. 2014-152394, filed on Jul. 25, 2014, the disclosures of which are incorporated herein by reference in their entireties for all purposes.

TECHNICAL FIELD

The present invention relates to a technique for detection, isolation and the like of memory invariant NKT cells by using a marker specific to the memory invariant NKT cells.

BACKGROUND ART

Innate lymphocytes such as NK, invariant natural killer T (iNKT) cells and γδ T cells mount rapid effector responses and therefore are important sentinels of the innate immune system and until recently were thought to be short-lived. Memory type NK cells have been identified and intensively studied in several systems (non-patent documents 1-4). In murine cytomegalovirus (MCMV) infection, Ly49H[+] NK cells have been found to be long-lived and to have a role in shaping prolonged anti-viral-specific NK cell responses and also to possess "memory" of previously encountered pathogens. Results of a global transcriptional analysis in the immunological genome project showed common memory transcripts and some shared markers of NK cells and CD8[+] T cells, suggesting conservation between the NK cell and CD8[+] T cell lineages of some activation mechanisms (non-patent document 5). In addition, memory γδT cells capable of simultaneously producing IFN-γ and IL-17 in the intestinal tissues have recently been identified (non-patent document 6).

iNKT cells express an invariant T cell antigen receptor (TCR) α-chain that is the product of a canonical rearrangement between the Vα14 (Vα24 in human) and the Jα18 gene segments, with a CDR3α region that is invariant at the amino acid level. These iNKT cells recognize a complex of the antigen-presenting MHC-like molecule CD1d and a glycolipid and secrete cytokines in an antigen-specific manner following engagement of their TCR (non-patent documents 7-10). The synthetic iNKT ligand (also referred to as iNKT ligand or CD1d ligand), α-galactosylceramide (α-GalCer) can be loaded (or "pulsed") onto CD1d-expressing cells such as, in addition to dendritic cells (DCs), CD1d-transfected tumor cells and fibroblasts (non-patent documents 11-13). By α-GalCer loaded CD1d-positive cells (CD1d[+] cells), iNKT cells are activated and capable of producing large quantities of interferon-γ (IFN-γ) (non-patent documents 11-13).

Immunotherapies utilizing the activation of iNKT cells (iNKT cell activation therapy) have heretofore been developed. One of them is a method aiming at functional recovery of the iNKT cells in the body of patients, which includes growing iNKT cells obtained from the patients in vitro and returning them to the body. Another method aiming at activation of iNKT cells by loading dendritic cell (DC) collected from the peripheral blood of patient with α-GalCer (DC/Gal) and returning same to the body of the patients has been developed and is also called a dendritic cell therapy. The safety and effect of this method has been verified by clinical tests (non-patent documents 14-17).

In addition, a new cell preparation for immunity induction using CD1d-positive cells, which causes activation of iNKT cells and maturation of DCs has been developed (patent document 1).

DOCUMENT LIST

Patent Document

[patent document 1] WO 2007/097370

Non-Patent Documents

[non-patent document 1] O'Leary, J. G., Goodarzi, M., Drayton, D. L. & von Andrian, U. H. T cell- and B cell-independent adaptive immunity mediated by natural killer cells. Nat Immunol 7, 507-516 (2006).

[non-patent document 2] Sun, J. C., Beilke, J. N. & Lanier, L. L. Adaptive immune features of natural killer cells. Nature 457, 557-561 (2009).

[non-patent document 3] Min-Oo, G., Kamimura, Y., Hendricks, D. W., Nabekura, T. & Lanier, L. L. Natural killer cells: walking three paths down memory lane. Trends Immunol 34, 251-258 (2013).

[non-patent document 4] Cooper, M. A. et al. Cytokine-induced memory-like natural killer cells. Proc Natl Acad Sci USA 106, 1915-1919 (2009).

[non-patent document 5] Bezman, N. A. et al. Molecular definition of the identity and activation of natural killer cells. Nat Immunol 13, 1000-1009, (2012).

[non-patent document 6] Sheridan, B. S. et al. γδT cells Exhibit Multifunctional and Protective Memory in Intestinal Tissues. Immunity 39, 184-195 (2013).

[non-patent document 7] Cerundolo, V., Silk, J. D., Masri, S. H. & Salio, M. Harnessing invariant NKT cells in vaccination strategies. Nat Rev Immunol 9, 28-38 (2009).

[non-patent document 8] Godfrey, D. I., Stankovic, S. & Baxter, A. G. Raising the NKT cell family. Nat Immunol 11, 197-206 (2010).

[non-patent document 9] Fujii, S. et al. Adjuvant activity mediated by iNKT cells. Semin Immunol 22, 97-102 (2010).

[non-patent document 10] Berzins, S. P., Smyth, M. J. & Baxter, A. G. Presumed guilty: natural killer T cell defects and human disease. Nat Rev Immunol 11, 131-142 (2011).

[non-patent document 11] Fujii, S., Shimizu, K., Kronenberg, M. & Steinman, R. M. Prolonged interferon-γδ producing NKT response induced with α-galactosylceramide loaded dendritic cells. Nat. Immunol. 3, 867-874 (2002).

[non-patent document 12] Shimizu, K., Goto, A., Fukui, M., Taniguchi, M. & Fujii, S. Tumor cells loaded with α-galactosylceramide Induce innate NKT and NK cell-dependent resistance to tumor implantation in mice. J. Immunol. 178, 2853-2861 (2007).

[non-patent document 13] Fujii, S., Goto, A. & Shimizu, K. Antigen mRNA-transfected, allogeneic fibroblasts loaded with NKT-cell ligand confer antitumor immunity. Blood 113, 4262-4272 (2009).

[non-patent document 14] Nieda, M. et al. Therapeutic activation of Vα24+Vβ11+ NKT cells in human subjects results in highly coordinated secondary activation of acquired and innate immunity. Blood 103, 383-389 (2004).

[non-patent document 15] Chang, D. H. et al. Sustained expansion of NKT cells and antigen-specific T cells after injection of α-galactosyl-ceramide loaded mature dendritic cells in cancer patients. J. Exp. Med. 201, 1503-1517 (2005).

[non-patent document 16] Motohashi, S. & Nakayama, T. Natural killer T cell-mediated immunotherapy for malignant diseases. Front Biosci (Schol Ed) 1, 108-116 (2009).

[non-patent document 17] Motohashi, S. et al. A phase I-II study of α-galactosylceramide-pulsed IL-2/GM-CSF-cultured peripheral blood mononuclear cells in patients with advanced and recurrent non-small cell lung cancer. J Immunol 182, 2492-2501 (2009).

SUMMARY OF THE INVENTION

Problems to be Solved by the Invention

In various iNKT cell activation therapies, while the action mechanism of immunity induction is different, the responsiveness of patients to the administered cells can be an index of a treatment effect since administered cells induce immunity. For example, in an iNKT cell activation therapy using DC/Gal, the responsiveness of patients to the administered DC/Gal is evaluated based on the number of iNKT cells or an induced IFN-γ production ability of iNKT cells in the patient after DC/Gal administration. However, the correlation between the number of iNKT cells and the responsiveness of patients is not clearly elucidated. In addition, evaluation of the IFN-γ production ability of iNKT cells accompanies a complicated operation since it requires collection of iNKT cells from the administration subject and in vitro culture thereof. Therefore, it is important to establish an easy method for the evaluation of the responsiveness of patients in iNKT cell activation therapy.

The present invention aims to provide a technique for specifically detecting and separating a long-term sustainable functional iNKT cell that predominantly produces IFN-γ after induction of the activation of the iNKT cell.

Means of Solving the Problems

The present inventors have conducted intensive studies and found that a functional iNKT cell, which is maintained for a long term, is present in the lung of the subject administered with a CD1d$^+$ cell loaded (pulsed) with an iNKT ligand, and the iNKT cell has the characteristics of memory cell. After proliferation and subsequent reduction phase, KLRG1-expressing iNKT cells were specifically maintained for several months as memory cells and showed protective immunoactivity for a long time. The KLRG1-expressing iNKT cells showed a stronger secondary response in an antigen-specific manner and produced a large amount of IFN-γ.

The inventions have further studied based on the above-mentioned finding and completed the present invention.

Accordingly, the present invention is as follows:

[1] A method of detecting a memory invariant NKT cell, comprising detecting the expression of KLRG1 in invariant NKT cells.

[2] The method of [1], wherein the expression of KLRG1 is detected by using an antibody that specifically recognizes KLRG1.

[3] A method of predicting the responsiveness of a patient to an iNKT cell activation therapy, which comprises
(1) measuring changes in the number of KLRG1-positive invariant NKT cells in a biological sample derived from a target patient, by administration of a CD1d-positive cell pulsed with an invariant NKT cell ligand; and
(2) correlating changes in the number of KLRG1-positive invariant NKT cells measured in (1), and responsiveness of the patient to an anti-tumor therapy with an antigen-presenting cell pulsed with an invariant NKT cell ligand.

[4] The method of [3], wherein the changes in the number of KLRG1-positive invariant NKT cells are measured using an antibody that specifically recognizes KLRG1.

[5] A method of isolating a memory invariant NKT cell, comprising isolating a KLRG1-positive and invariant NKT cell receptor-positive cell fraction from a lymphocyte-containing sample.

[6] The method of [5], wherein the KLRG1-positive and invariant NKT cell receptor-positive cell is isolated using an antibody that specifically recognizes KLRG1 and a soluble CD1d pulsed with an invariant NKT cell ligand.

[7] A reagent for the detection of a memory invariant NKT cell, comprising an antibody that specifically recognizes KLRG1.

[8] The reagent of [7], further comprising a soluble CD1d pulsed with an invariant NKT cell ligand.

[9] A diagnostic reagent for the prediction of responsiveness of a patient to an anti-tumor therapy with an antigen-presenting cell pulsed with an invariant NKT cell ligand, which comprises an antibody that specifically recognizes KLRG1.

[10] The reagent of [9], further comprising a soluble CD1d pulsed with an invariant NKT cell ligand.

[11] A reagent for the isolation of a memory invariant NKT cell, comprising an antibody that specifically recognizes KLRG1, and a soluble and pulsed with an invariant NKT cell ligand.

[12] An antibody that specifically recognizes KLRG1, or a combination of the antibody and a soluble CD1d pulsed with an invariant NKT cell ligand, for use in the prediction of responsiveness of a patient to an anti-tumor therapy with an antigen-presenting cell pulsed with an invariant NKT cell ligand.

[13] Use of an antibody that specifically recognizes KLRG1, or a combination of the antibody and a soluble CD1d pulsed with an invariant NKT cell ligand, for the production of a diagnostic reagent for the prediction of responsiveness of a patient to an anti-tumor therapy with an antigen-presenting cell pulsed with an invariant NKT cell ligand.

Effect of the Invention

According to the present invention, detection of a KLRG1-expressing iNKT cell enables evaluation of the state of activation of iNKT cell of a patient easily, the presence or absence of immune defense by iNKT cells over a long time, and responsiveness of the patient to an iNKT cell activation therapy.

BRIEF DESCRIPTION OF THE DRAWINGS

FIG. 1-a shows frequency of iNKT cells in the spleen and lung. B16 melanoma cells ($2\times10^5$ cells/mouse) were administered i.v. to C57BL/6 mice. At day 7, B16-bearing or naïve mice were immunized with $1\times10^6$ DC/Gal(FIG. 1-a-FIG. 1-e). The frequency of iNKT cells was assessed in the four groups of mice at day 14.

FIG. 1-b shows the number of iNKT cells in the lung. The number of iNKT cells in lung was assessed in the four groups of mice at day 14. *P<0.05 naïve or B16 versus DC/Gal or B16-DC/Gal, three independent experiments (mean±SEM).

FIG. 1-c shows IFN-γ production by lung iNKT cells by α-GalCer re-stimulation. IFN-γ production by lung iNKT cells was measured by ELISPOT assay at day 14 in the four groups of mice in response to re-stimulation with α-GalCer (100 ng/ml) for 16 h.

FIG. 1-d shows cytotoxicity of lung MNCs against B16 melanoma. Cytotoxicity assay against B16 melanoma was assessed a week after a treatment with DC/Gal. Tumor cells as targets were mixed with pooled lung MNCs from naïve or DC/Gal-injected mice at various E:T ratios for 16 h. E/T=10, E/T=30, E/T=100 from the left. *P<0.05 naïve v.s. DC/Gal or B16-DC/Gal.

FIG. 1-e shows microarray analysis of splenic iNKT cells. Microarray analysis of splenic iNKT cells was carried out for naïve (n=3) and DCG immunized mice (n=4). Data are representative of two separate experiments with similar results (mean±SEM, n≥4 per group)

FIG. 2-a shows expression of KLRG1 on iNKT cell surface. C57BL/6 mice were immunized with DC/Gal (bottom) or were untreated (top and bottom left). Seven days later, the expression of KLRG1 by iNKT cells was analyzed by gating on $CD19^-CD1d$-dimer/$Gal^+$ cells.

FIG. 2-b shows flow cytometric analysis of the surface phenotype of $KLRG1^+$ and $KLRG1^-$ iNKT cells in the lung of mouse immunized with naïve or DC/Gal.

FIG. 2-c shows frequency of $KLRG1^+$iNKT cells. The frequency of KLRG1+ iNKT cells was analyzed from day 2 to 12 weeks after immunization with DC/Gal.

FIG. 2-d shows changes in the absolute number of total iNKT cells in each organ from day 5 to 90 after immunization with DC/Gal. Data are representative of two separate experiments (n≥4 per group).

FIG. 2-e shows changes in the percentages of $KLRG1^+$ iNKT cells in each organ from day 5 to 90 after immunization with DC/Gal. Data are representative of two separate experiments (n≥4 per group).

FIG. 3-a shows gene expression analysis in $KLRG1^+$ iNKT cells and $KLRG1^-$iNKT cells. C57BL/6 mice were immunized with DC/Gal or were untreated. One month later, $KLRG1^+$ or $KLRG1^-$ iNKT cells in the lung were purified by FACS. Quantitative analyses of gene expression for cytokines, chemokines, granzyme A (gzma) and Fas ligand (fasL) were performed. Expression of each mRNA in purified iNKT cells was determined by quantitative real-time PCR and is depicted as the number of transcripts per one copy of the housekeeping gene HPRT. Data are shown as representative of two independent experiments with 4 mice per group with triplicates (mean±SEM).

FIG. 3-b shows granzyme A expression in $KLRG1^+$ or $KLRG1^-$ iNKT cells. The expression of granzyme A in $KLRG1^+$ or $KLRG1^-$ iNKT cells in the lung of mice immunized with or without DC/Gal were analyzed after stimulation with plate-bound anti-CD3 Ab plus soluble anti-CD28 Ab for 2 h in the presence of brefeldin A for intracellular staining of IFN-γ. Analysis gates were set on $CD19^-$ CD1d-dimer/$Gal^+$ cells. Data are shown as representative of two independent experiments with 4 mice.

FIG. 3-c shows IFN-γ expression in $KLRG1^+$ or $KLRG1^-$ iNKT cells. The expression of IFN-γ in $KLRG1^+$ or $KLRG1^-$ iNKT cells in the lung of mice immunized with or without DC/Gal were analyzed after stimulation with plate-bound anti-CD3 Ab plus soluble anti-CD28 Ab for 2 h in the presence of brefeldin A for intracellular staining of IFN-γ. Analysis gates were set on $CD19^-$ CD1d-dimer/$Gal^+$ cells. Data are shown as representative of two independent experiments with 4 mice.

FIG. 3-d shows IFN-γ, cc13 and cc14 production of $KLRG1^+$ or $KLRG1^-$iNKT cells. Conditions are the same as in FIG. 3-c, the supernatants from the cultures with plate-bound anti-CD3 Ab plus soluble anti-CD28 Ab for 24 h were analyzed at the protein level for IFN-γ by ELISA, CCL3 and CCL4 by Luminex. Data are shown as representative of two independent experiments with 4 mice per group with triplicates (mean±SEM). *P<0.05 naïve $KLRG1^-$ or DC/Gal $KLRG1^-$ iNKT v.s. DC/Gal $KLRG1^+$ iNKT.

FIG. 3-e shows transcription factor expression in $KLRG1^+$ or $KLRG1^-$iNKT cells. Expression of the transcription factors Eomes, Runx3, Tbx21, Gata3 and Rorc by $KLRG1^+$ and $KLRG1^-$ iNKT cells from the lungs of mice given DC/G one month previously were analyzed by real time PCR. Data are shown as representative of two independent experiments with 4 mice per group with triplicates (mean±SEM).

FIG. 3-f shows IFN-γ expression in $KLRG1^+$ or $KLRG1^-$ iNKT cells. Mice that had been immunized with DC/Gal were challenged with B16 melanoma 4 months later. IFN-γ secretion assay for B16 reactive iNKT cells was performed 12 h later vaccinated with or without DC/Gal.

FIG. 3-g shows the number of metastasis in the lung in DC/Gal immune or non-immune mouse challenged with B16 melanoma. Conditions are the same as those in FIG. 3-f. Antitumor effects were evaluated 2 weeks later by counting the number of metastases in the lungs. Some mice were treated with anti-NK1.1 Ab just prior to challenge with B16. Data are means obtained from two independent experiments with 4-6 mice per group.

FIG. 4-a shows profiles of BrdU incorporation by $KLRG1^+$iNKT cells. Groups of naïve or DC/Gal-immune B6 animals were given BrdU on day 0 (i.v.) and BrdU in the drinking water until day 7 and then analyzed one month later, gating on the $CD19^-CD1d$-dimer/$Gal^+$ cells. Data are representative of two separate experiments (n=3 per group).

FIG. 4-b shows the number of $KLRG1^+$iNKT cells in the liver and lung of Jα18-KO mouse adoptively transferred with $KLRG1^+$iNKT cells. $KLRG1^+$iNKT cells were sorted from $Vα14^+$NKT cloned mice that had been immunized with DC/Gal 1 month previously. $KLRG1^+$iNKT cells ($1×10^5$/mouse) were transferred into Jα18-KO mice. The mice were treated with or without DC/Gal 4 weeks later. The frequency of $KLRG1^+$iNKT cells was analyzed a week later. Data are representative of two separate experiments (n=4 per group).

FIG. 4-c shows the number of $Vα1^+venus^+$ cloned iNKT cells in the liver and lung of B6 mouse adoptively transferred with naïve iNKT cells from $Vα1^+$iNKT cloned mice. Naïve iNKT cells ($KLRG1^-$ iNKT cells) from $Vα1^+$iNKT cloned mice were transferred into C57BL/6 mice, which were immunized with DC/Gal on the same day. Three months later, the mice were again treated with or without DC/Gal. The number of $Vα14^+venus^+$ cloned iNKT in all three groups were assessed in the liver and lung a week later.

FIG. 4-d shows frequency of $KLRG1^+$ iNKT cells in the liver and lung of B6 mouse adoptively transferred with naïve iNKT cells from $Vα14^+$iNKT cloned mice. Test conditions are the same as those in FIG. 4-c. The frequency of $KLRG1^+$ iNKT cells was analyzed a week later.

FIG. 4-e shows the number of $KLRG1^+$ iNKT cells in the liver and lung of B6 mouse adoptively transferred with naïve iNKT cells from $Vα14^+$iNKT cloned mice. Test conditions are the same as those in FIG. 4-c. The number of KLRG1+ iNKT cells was analyzed a week later.

FIG. 5-a shows the number of KLRG1+ iNKT cells in the lung of mouse immunized with DC pulsed with various NKT ligands. C57BL/6 mice were administered with DC; 10 ng/ml or 100 ng/ml α-GalCer-pulsed DC (DC/Gal (10), DC/Gal (100)); and 10 µg/ml iGB3 or GSL-pulsed DC (DC/iGB3 and DC/GSL). Some mice immunized with DC/Gal (100) were rechallenged with DC/Gal (10), DC/Gal (100), DC/iGB3 and DC/GSL 2 months later. The number of KLRG1+ iNKT cells in the lung was measured by flow cytometry after gating on CD19− cells using CD1d-dimer/Gal-APC and KLRG1-PE/cy7. Data are representative of two separate experiments (mean±SEM) (n=4-6 per group).

FIG. 5-b shows analysis results of Vβ use in iNKT cells. Test conditions are the same as a panel A. Immunized mice were analyzed for iNKT cell TCR Vβ usage using TCR Vβ-FITC and CD1d-dimer/Gal-APC and KLRG1-PE/cy7.

FIG. 5-c shows heatmaps showing the cluster size in each Vβ repertoire. The naïve iNKT cells and KLRG1+ iNKT cells for TCR RNA-seq analysis were prepared from pooled iNKT cells from 5-6 naïve or DC/Gal-immunized mice. The complementary-determining region 3 of Vβ (CDR3β) was assessed by a GS Junior system (Roche) in naïve, DC/Gal-injected mice (d7, d2) or DC/Gal-DC/Gal boosted mice (each stage, n=2). The clusters of high-frequency (top50) of CDR3 in each Vβ repertoire in the boosted mice were selected and then clustered among those in naïve, DC/Gal-injected mice (d7, d2) or DC/Gal-DC/Gal boosted mice.

FIG. 5-d shows the size distributions of CDR3β clusters in each Vβ repertoire of respective mice are shown. The numbers of clusters with the size not less than and less than 1% of the total sequence reads are expressed as right and left bars, respectively.

FIG. 5-e shows principal component analysis performed for whole clusters of CDR3 is shown. Two groups of CDR3 clusters were identified (i). The Cluster size distributions of KLRG1+iNKT cells in the groups (1) and (2) are shown as bar graphs, respectively (ii and iii).

DESCRIPTION OF EMBODIMENTS

The present invention provides a detection method of a memory invariant natural killer T cell (also referred to as long-term sustainable functional iNKT cell, memory iNTK cell).

NKT cell is a kind of lymphocyte expressing two antigen receptors, i.e., T cell receptor (TCR) and NK receptor. The repertoire of T cell receptors on NKT cells, unlike on ordinary T cells, are extremely limited. For example, the α chain of the T cell receptor on mouse NKT cells (sometimes referred to as Vα14NKT cells) is encoded by invariant Vα14 and Jα18 gene segments (Proc Natl Acad Sci USA, 83, p. 8708-8712, 1986; Proc Natl Acad Sci USA, 88, p. 7518-7522, 1991; J Exp Med, 180, p. 1097-1106, 1994) and a chain of T cell receptor on human NKT cell is encoded by invariant Vα24 and Jα18 gene segments having high homology with mouse Vα14. An NKT cell having such invariant Vα chain (e.g., mouse:Vα14, human:Vα24) is particularly referred to as an iNKT cell. In iNKT cell, a T cell receptor on the cell (this is referred to as iNKT cell receptor) recognizes the following "iNKT cell ligand" presented on the CD1d molecule. Such properties are particularly referred to as CD1d-restricted.

The "memory invariant NKT cell (long-term sustainable functional iNKT cell)" refers to an iNKT cell that has undergone stimulation by an iNKT cell ligand presented on a CD1d molecule, and is maintained in vivo after undergoing clonal proliferation by the stimulation and subsequent contraction phase. In contrast, an iNKT cell that has not undergone stimulation by an iNKT cell ligand presented on a CD1d molecule is referred to a "naïve invariant NKT cell". The response of the memory iNKT cell to the stimulation by an iNKT cell ligand presented on a CD1d molecule is enhanced as compared to the naïve iNKT cell, and the memory iNKT cell produces a large amount of IFN-γ in response to the stimulation by an iNKT cell ligand presented on a CD1d molecule. In one embodiment, the memory iNKT cell expresses granzyme A at a higher level as compared to the naïve iNKT cell, and has a high anti-tumor activity.

The memory iNKT cells detected in the present invention are derived from mammal. Examples of the mammal include rodents (e.g., mouse, rat, hamster, guinea pig and the like), order Logomorpha such as rabbit and the like, order Ungulata such as swine, bovine, goat, horse, sheep and the like, order Carnivora such as dog, cat and the like, primates such as human, monkey, *Macaca mulatta, Macaca fascicularis*, marmoset, orangutan, chimpanzee and the like, and the like. The mammal is preferably rodent (mouse etc.) or primate (human etc.).

The detection method of the present invention includes detection of the expression of a discrimination marker such as KLRG1 and the like in iNKT cells. The present invention is based on the finding that, while particular genes such as KLRG1 and the like are specifically expressed in memory iNKT cell, naïve iNKT cells do not express particular genes such as KLRG1 and the like, and particular genes such as KLRG1 and the like are useful as a specific marker capable of discriminating memory iNKT cells from naïve iNKT cells.

Since memory iNKT cells specifically express KLRG1, cc13, cc14 and granzyme A, they can be discriminated from naïve iNKT cell by confirming the expression of KLRG1, cc13, cc14 and/or granzyme A in iNKT cells.

From the above, discrimination marker(s) of memory iNKT cell is KLRG1, cc13, cc14 and/or granzyme A, preferably KLRG1.

In one embodiment, in memory iNKT cells, high expression levels of CD43, CD49d, Ly6C, NKG2D, FasL and/or IFN-γ are continued as compared to naïve iNKT cells, and low expression levels of CD69, CD127 and/or CD27 are confirmed as compared to naïve iNKT cells. Furthermore, the characteristic of memory iNKT cell is no detection or remarkably low expression levels of the expression of LPAM-1, Ly49D and/or Ly49H unlike NK cells.

Therefore, a method of detecting the expression level(s) CD43, CD49d, Ly6C, NKG2D, CD69, CD127, CD27, LPAM-1, Ly49D and/or Ly49H in addition to the discrimination markers of the above-mentioned memory iNKT cell can be utilized for the judgment of the discrimination of memory iNKT cells.

The sample to be subjected to the detection method of the present invention is not particularly limited as long as it is a biological sample possibly containing a memory iNKT cell. Preferably, peripheral blood, bone marrow, thymus, lymph node, lung, liver, tissue such as tumor tissue and the like, a mononuclear cell fraction isolated therefrom and the like are used.

A discrimination marker for memory iNKT cell may also be expressed in cells other than memory iNKT cells. Therefore, unless purified iNKT cell or a cell line established from iNKT cell is used as a sample, it is generally necessary to discriminate iNKT cell from other cells in the sample.

As a method for discriminating iNKT cells from other cells in the sample, those skilled in the art can appropriately select a method from known ones, such as a method including flow cytometry using NKT ligand-CD1d dimer or tetramer (which is a cell surface marker of iNKT cell) complex positive (Va24+Vb11+, 6B11-positive for human) as an index.

As a method for discriminating iNKT cells, a method utilizing an iNKT cell ligand can also be mentioned. Since iNKT cell specifically recognizes iNKT cell ligands presented on a CD1d molecule via an iNKT cell receptor, iNKT cells are discriminated from other cells in the sample by detecting the expression of the iNKT cell receptor on the cell surface by, for example, using a soluble CD1d pulsed with the iNKT cell ligand. Soluble CD1d pulsed with the iNKT cell ligand specifically binds to iNKT cells. Therefore, iNKT cells are discriminated from other cells in the sample as "soluble CD1d pulsed with an invariant NKT cell ligand"-positive cells.

In another embodiment, iNKT cells can be discriminated from other cells by co-culturing the harvested sample with CD1d-expressing cells pulsed with iNKT cell ligand, proliferating the iNKT cells to increase the proportion of iNKT cells in the sample, and performing the aforementioned flow cytometry method, a method using a soluble CD1d and the like.

Invariant NKT cell ligand (also referred to as iNKT cell ligand, CD1d ligand) refers to a compound specifically recognized by a T cell receptor (iNKT cell receptor) on the iNKT cell when presented on a CD1d molecule, which can specifically activate the iNKT cell. Examples of the "invariant NKT cell ligand" used in the present invention include α-glycosylceramide, isoglobotrihexosylceramide (iGB3) (Science, 306, p. 1786-1789, 2004), OCH (Nature 413:531, 2001), GSL of *Sphingobium yanoikuyae* and the like. α-Glycosylceramide is a sphingoglycolipid wherein saccharide such as galactose, glucose and the like is bonded to ceramide at the α configuration, and examples thereof include those disclosed in WO93/05055, WO94/02168, WO94/09020, WO94/24142, WO98/44928, Science, 278, p. 1626-1629, 1997 and the like. Of those, (2S,3S,4R)-1-O-(α-D-galactopyranosyl)-2-hexacosanoylamino-1,3,4-octadecanetriol (to be referred to as α-galactosylceramide or α-GalCer in the present specification) or α-galactosylceramide analog is preferable. Examples of the α-galactosylceramide analog include, but are not limited to, the compounds described in WO 2007/099999 (U.S. Pat. No. 8,163,705), WO 2009/119692 (U.S. Pat. No. 8,551,959), WO 2008/102888 (U.S. Pat. No. 8,299,223), WO 2010/030012 (U.S. Pat. No. 8,580,751), WO 2011/096536 (U.S. Pat. No. 8,853,173), and WO 2013/162016 (US-A-2015-0152128).

Soluble CD1d refers to an extracellular domain of CD1d, which has an iNKT cell ligand presentation activity. To enhance affinity for iNKT cells, it is preferable to use a multimer of soluble CD1d (J Exp Med, 192, p. 741-754, 2000; J Exp Med, 191, p. 1895-1903, 2000). Examples of the multimer include dimer-octamer, preferably, tetramer or dimer.

"Pulse of soluble CD1d with an invariant NKT cell ligand" refers to placing an iNKT cell ligand on soluble CD1d in a manner that allows the ligand to be presented to iNKT cells. Pulse of soluble CD1d with an invariant NKT cell ligand can be achieved by bringing the iNKT cell ligand into contact with the soluble CD1d. For example, soluble CD1d is incubated in a physiological aqueous solution containing an iNKT cell ligand. In this case, the concentration of the iNKT cell ligand in the aqueous solution can be set as appropriate according to the kind of the iNKT cell ligand, and is, for example, 1 to 10000 ng/ml, preferably 10 to 1000 ng/ml. Furthermore, after incubation, by removing the free iNKT cell ligand by gel filtration and the like, soluble CD1d pulsed with the iNKT cell ligand are isolated.

Soluble CD1d pulsed with the iNKT cell ligand may be labeled with an appropriate fluorescent dye such as FITC, PE and the like, biotin and the like to enable easy detection in the flow cytometric analysis.

In a preferable embodiment, a soluble CD1d pulsed with the iNKT cell ligand is a soluble CD1d tetramer or dimer pulsed with α-GalCer.

KLRG1 (Killer cell lectin-like receptor subfamily G, member 1) is a known type II transmembrane glycoprotein, and the amino acid sequence thereof is also known. KLRG1 that can be used in the present invention is KLRG1 of the aforementioned mammals. Representative amino acid sequences of human KLRG1 include NCBI integrated database Accession No. NP_005801, version NP_005801.3 (updated on Jan. 26, 2014) is known. As a representative amino acid sequence of mouse KLRG1, NCBI integrated database Accession No. NP_058666, version NP_058666.1 (updated on Feb. 26, 2014) is known. As a representative mRNA (cDNA) sequence of human KLRG1, NCBI integrated database Accession No. NM_005810, version NM_005810.3 (updated on Mar. 15, 2015) is known. As a representative mRNA (cDNA) sequence of mouse KLRG1, NCBI integrated database Accession No. NM_016970, version NM_016970.1 (updated on Feb. 15, 2015) is known.

Detection of a memory iNKT cell discrimination marker in iNKT cells is generally carried out ex vivo.

A method for confirming the expression level of the discrimination marker of memory iNKT cell is explained taking KLRG 1 as an example. As for identification markers other than KLRG1, it is also possible to confirm the expression levels and perform the present invention in the same manner as for KLRG1. The expression levels of KLRG1 (polypeptide) can be measured by an immunochemical method using an antibody that specifically recognizes KLRG1. As the immunochemical method, flow cytometric analysis, radioisotope immunoassay method (RIA method), ELISA method (Methods in Enzymol. 70: 419-439 (1980)), Western blotting, immunohistostaining and the like can be mentioned. KLRG1 is a type II transmembrane protein, and is expressed on a cell surface. Therefore, it is convenient to detect the expression of KLRG1 on the cell surface of iNKT cell by flow cytometric analysis and the like.

An antibody that specifically recognizes KLRG1 can be produced by an existing general production method using a KLRG1 polypeptide or a partial peptide having antigenicity thereof as an immunogen. In the present invention, the antibody that specifically recognizes the KLRG1 extracellular domain is preferably used. In the present invention, the antibody includes, but is not limited to natural antibody such as polyclonal antibody, monoclonal antibody (mAb) and the like, chimeric antibody that can be produced using a gene recombination technique, humanized antibody, single strand antibody, and binding fragments thereof. Preferably, the antibody is polyclonal antibody, monoclonal antibody or a binding fragment thereof. A binding fragment means a region of a part of the aforementioned antibody having specific binding activity, and specific examples thereof include F(ab')$_2$, Fab', Fab, Fv, sFv, dsFv, sdAb and the like (Exp. Opin. Ther. Patents, Vol. 6, No. 5, p. 441-456, 1996). The class of the antibody is not particularly limited, and antibodies having any isotype such as IgG, IgM, IgA, IgD or IgE and the like are also encompassed. Preferably, it is IgG or IgM, and more preferably IgG in consideration of the easiness of purification and the like.

An antibody that specifically recognizes KLRG1 may be labeled with an appropriate fluorescent dye such as FITC, PE, and the like, biotin and the like, so that it can be easily detected by flow cytometric analysis.

The "specific recognition" of antigen X by an antibody means that the binding affinity of the antibody for antigen X in antigen-antibody reaction is higher than that for a non-specific antigen (e.g., bovine serum albumin (BSA)).

As the expression level of KLRG1, the expression level of KLRG1 mRNA may be measured. The expression level of KLRG1 mRNA can be measured by a well-known molecular biological method such as PCR (RT-PCR, real-timePCR etc.), Northern blotting, nucleic acid array, in situ hybridization and the like by using a nucleic acid primer or a nucleic acid probe that specifically detects KLRG1 mRNA or cDNA.

As a nucleic acid probe capable of specifically detecting KLRG1 mRNA or cDNA, a polynucleotide comprising a contiguous nucleotide sequence of about 15 bases or more, preferably about 18 to about 500 bases, more preferably about 18 to about 200 bases, even more preferably about 18 to about 50 bases, which is contained in the nucleotide sequence of KLRG1 mRNA or cDNA, or a complementary sequence thereof can be mentioned.

A nucleic acid primer capable of specifically detecting KLRG1 mRNA or cDNA may be any as long as it is designed to be able to specifically amplify a part or all of the region of KLRG1 mRNA or cDNA. For example, a pair of polynucleotides of a combination of a polynucleotide containing a nucleotide sequence of about 15-about 50 bases, preferably about 18-about 30 bases, which hybridizes to a part of the complementary sequence of the nucleotide sequence of KLRG1 mRNA or cDNA, and a polynucleotide containing a nucleotide sequence of about 15-about 50 bases, preferably about 18-about 30 bases, which hybridizes to a part of the above-mentioned nucleotide sequence on the 3' side from said hybridization site (whereby a nucleic acid of a fragment length of about 50-about 1,000 bases, preferably about 50-about 500 bases, more preferably about 50-about 200 bases is amplified), can be mentioned.

The nucleic acid probe and the nucleic acid primer may contain additional sequences (nucleotide sequences not complementary to the detection target polynucleotide) as long as they do not interfere with the specific detection.

In addition, the nucleic acid probe and the nucleic acid primer may be labeled with a suitable label, such as radioisotope (e.g., $^{125}$I, $^{131}$I, $^{3}$H, $^{14}$C, $^{32}$P, $^{33}$P, $^{35}$S etc.), enzyme (e.g., β-galactosidase, β-glucosidase, alkaline phosphatase, peroxidase, malate dehydrogenase etc.), fluorescent substance (e.g., fluorescamine, fluorescein isothiocyanate etc.), luminescent substance (e.g., luminol, luminol derivative, luciferin, lucigenin etc.), biotin and the like. Alternatively, a quencher (quenching substance) that absorbs the fluorescence energy emitted by the fluorescent substance may be further bound to the vicinity of a fluorescent substance (e.g., FAM, VIC etc.). In such embodiment, the fluorescent substance and the quencher are separated and the fluorescence is detected during the detection reaction.

The nucleic acid probe and the nucleic acid primer may be DNA or RNA, and may be a single strand or a double strand. When they are double-stranded, they may be any of a double-stranded DNA, a double-stranded RNA and a DNA/RNA hybrid.

The above-mentioned nucleic acid probe and the nucleic acid primer can be synthesized by, for example, a conventional method using a DNA/RNA automatic synthesizer based on the KLRG1 mRNA or cDNA nucleotide sequence information provided in a known gene sequence database.

In the detection method of the present invention, when the expression of a discrimination marker such as KLRG1 and the like is detected in iNKT cells (that is, when positive to a discrimination marker such as KLRG1 etc.), the cell is identified as a memory iNKT cell.

In one embodiment, the detection method of the present invention includes detecting the expression of an iNKT cell receptor and a discrimination marker of a memory iNKT cell on the cell surface of the cells contained in the target sample to be evaluated. In the embodiment, an iNKT cell receptor-positive and memory iNKT cell discrimination marker-positive (preferably KLRG1-positive) cell is identified as a memory iNKT cell.

Using the detection method of the present invention, a memory iNKT cell can be easily detected, and therefore, the responsiveness of the patient to an iNKT cell activation therapy can be predicted by utilizing same. That is, the present invention provides a method of predicting the responsiveness of a patient to an iNKT cell activation therapy, which comprises the following steps, (1) measuring changes in the number of discrimination marker (e.g., KLRG1 and the like)-positive invariant NKT cells in a biological sample derived from a target patient, by administration of a CD1d-positive cell pulsed with an invariant NKT cell ligand; and (2) correlating changes in the number of the discrimination marker (e.g., KLRG1 and the like)-positive invariant NKT cells measured in the above-mentioned (1), and responsiveness of the patient to the iNKT cell activation therapy.

In the present invention, the "iNKT cell activation therapy" refers to an immunotherapy utilizing the activation of iNKT cells, which is typically 1) a method of growing iNKT cells collected from a patient in vitro and returning them to the body for the purpose of functional recovery of the iNKT cells in the body of the patient, 2) a method of activating iNKT cells by loading an iNKT cell ligand on antigen presenting cells collected from the peripheral blood of a patient and returning them to the body of the patient again, or 3) a method of inducing activation of the innate immunity and acquired immunity by administering an artificially prepared CD1d-positive cell, which is loaded with an iNKT cell ligand, to a target.

An antigen-presenting cell refers to a cell that presents an antigen to lymphocytes to promote the activation of the lymphocytes. Usually, antigen-presenting cells are dendritic cells or macrophages capable of presenting an antigen to T cells or NKT cells. Particularly, dendritic cells have the potent capability of antigen presentation, and are capable of presenting an antigen via MHC Class I, MHC Class I-like molecules (CD1d and the like), MHC Class II and the like expressed on the cell surface, and activating T cells or NKT cells; therefore, dendritic cells are preferable. The antigen-presenting cells are preferably CD1d expressing cells in order to secure the presentation of an iNKT cell ligand to iNKT cells.

Useful antigen-presenting cells are those derived from an optionally chosen mammal. As the mammal, those mentioned above can be mentioned. Preferably, an antigen presenting cell of a mammal of the same species as the target patient is used. For example, when the patient is a human, a human antigen presenting cell is used.

Antigen-presenting cells in the body can be isolated from tissues (for example, lymph nodes, spleen, peripheral blood and the like) of the mammals mentioned above by a known method. For example, dendritic cells can be isolated using an antibody against a cell surface marker expressed specifically on antigen-presenting cells, by means of a cell sorter, panning, the antibody magnetic beads method and the like. When dendritic cells are isolated as antigen-presenting cells, for example, CD11c, MHC Class I, MHC Class I-like molecules (CD1 and the like), MHC Class II, CD8α, CD85k, CD86, FDL-M1, DEC-205 and the like can be used as cell surface markers expressed specifically on dendritic cells.

Antigen-presenting cells can also be produced by culturing bone marrow cells, mononuclear cells and the like of the mammals mentioned above under appropriate antigen-presenting cell differentiation conditions. For example, bone marrow cells, when cultured in the presence of GM-CSF (and IL-4 in some cases) for about 6 days, differentiate into dendritic cells (bone marrow-derived dendritic cells: BMDC) (Nature, 408, p. 740-745, 2000). By culturing mononuclear cells (particularly monocytes, macrophages and the like) in peripheral blood in the presence of GM-CSF (and IL-2 and/or IL-4 in some cases), dendritic cells can be obtained.

An artificially prepared CD1d-positive cell is a transfectant artificially expressing an antigen and CD1d gene by introducing same into any mammalian cell or mammalian cultured cell. The cell may be a syngenic, allogeneic or xenogeneic cell for the subject of administration. A CD1d-positive cell loaded with an iNKT cell ligand simultaneously induces activation of NKT cells and T cell immune response, which is a method for inducing very potent immunity against antigen (WO 2007/097370).

Hereinafter, both artificially-prepared CD1d-positive cell and antigen presenting cells are explained as "CD1d-positive cell".

"Pulse of CD1d-positive cell with an invariant NKT cell ligand" refers to placing an iNKT cell ligand on CD1d molecule on the cell surface in a manner that allows the ligand to be presented to iNKT cells. Pulse of CD1d-positive cell with an iNKT cell ligand can be achieved by bringing the iNKT cell ligand into contact with the CD1d-positive cells. For example, CD1d-positive cells are cultured in a physiological culture medium containing an iNKT cell ligand. In this case, the concentration of the iNKT cell ligand in the culture medium can be set as appropriate according to the kind of the iNKT cell ligand, and is, for example, 1 to 10000 ng/ml, preferably 10 to 1000 ng/ml. Furthermore, after cultivation, by washing the CD1d-positive cells with a culture medium or physiological aqueous solution free of an iNKT cell ligand to remove the free iNKT cell ligand, CD1d-positive cells pulsed with the iNKT cell ligand are isolated.

The disease to be the target of treatment by a CD1d-positive cell pulsed with an iNKT cell ligand includes tumor and infectious disease.

The type of tumor is not particularly limited as long as the iNKT cell ligand is therapeutically effective. Examples of the tumor include lung cancer (small and/or non-small cell), brain tumor, gastric cancer, esophagus cancer, liver cancer, pancreatic cancer, renal cancer, urinary bladder cancer, breast cancer, ovarian cancer, uterine cancer, testis cancer, skin cancer, osteosarcoma, colorectal cancer, chronic lymphocytic leukemia, acute lymphocytic leukemia, acute non-lymphatic leukemia, chronic myeloid leukemia, ACTH-producing tumor, adrenal cortex cancer, skin T cell lymphoma, endometrial carcinoma, Ewing sarcoma, gall bladder cancer, head and neck cancer, Hodgkin lymphoma, Kaposi's sarcoma, melanoma, mesothelioma, multiple myeloma, neuroblastoma, non-Hodgkin's lymphoma, ovary (germ cell) cancer, penile cancer, prostate cancer, retinoblastoma, soft tissue sarcoma, flat epithelial cell cancer, thyroid cancer, trophoblastic neoplasm, vaginal cancer, vulvar cancer, Wilms' tumor and the like.

Infectious disease refers to diseases caused by infection with pathogens, and includes, for example, viral infection caused by virus pathogens such as human immunodeficiency virus (HIV), hepatitisvirus (e.g., A-type, B-type, C-type, D-type and E-type hepatitis viruses), influenza virus, simple herpes virus, West Nile fever virus, human papilloma virus, encephalitis virus, human T cell leukemia virus (e.g., HTLV-I) and the like; protozoan infections caused by protozoa such as malaria, *Trypanosoma, Toxoplasma* and the like; bacterial infections caused by bacterium such as pneumococcus, typhoid bacilli, *shigella* and the like, and the like.

The target patient of the iNKT cell activation therapy is generally the aforementioned mammal, preferably rodents (mouse etc.) or primates (human etc.), more preferably human.

The responsiveness of a patient to the iNKT cell activation therapy refers to the extent or the presence or absence of induction of iNKT cell having an IFN-γ production ability in response to the administration of CD1d-positive cells pulsed with an iNKT cell ligand. As mentioned above, in an antitumor treatment by an iNKT cell activation therapy, since the number of iNKT cells capable of producing induced IFN-γ is positively correlated with a long-term anti-tumor effect, the higher the responsiveness of the patient (the number of iNKT cells capable of producing induced IFN-γ) is, the higher the therapeutic effect can be expected. Since the present inventors have shown that iNKT cells having an ability to produce IFN-γ induced by the administration of a CD1d-positive cells pulsed with an iNKT cell ligand are memory iNKT cells, the responsiveness of the patient to an iNKT cell activation therapy can be evaluated by detecting discrimination marker (e.g., KLRG1 and the like)-positive iNKT cells as memory cells, and monitoring changes in the number thereof, according to the above-mentioned detection method of the present invention.

In the prediction method of the present invention, changes in the number of KLRG1-positive iNKT cells in a biological sample derived from a target patient, due to the administration of a CD1d-positive cell pulsed with an iNKT cell ligand, is measured. To be specific, changes in the number of the discrimination marker (e.g., KLRG 1 and the like)-positive iNKT cells (i.e., memory iNKT cells) is measured by detecting the expression of a discrimination marker such as KLRG1 and the like in iNKT cells contained in a biological sample derived from a target patient, according to the above-mentioned detection method of the present invention. In one embodiment, changes in the number of discrimination marker (e.g., KLRG 1 and the like)-positive iNKT cells are measured by using an antibody that specifically recognizes a discrimination marker such as KLRG1 and the like or a nucleic acid primer or a nucleic acid probe that specifically detects mRNA or cDNA of a discrimination marker such as KLRG1 and the like. In a preferable embodiment, expression of iNKT cell receptor and a discrimination marker such as KLRG1 and the like on the cell surface of cells contained in a biological sample derived from a target patient is detected. In this embodiment, preferably, expression of an iNKT cell receptor and a discrimination marker such as KLRG1 and the like on the cell surface of the cell is detected using an antibody that specifically recognizes a discrimination marker such as KLRG1 and the like and a soluble CD1d pulsed with an iNKT cell ligand. Then, iNKT cell receptor-positive and discrimination marker (e.g., KLRG1 and the like)-positive iNKT cells are identified as discrimination marker (e.g., KLRG1 and the like)-positive iNKT cells (i.e., memory iNKT cells) and changes in the cell number are measured.

Changes in the number of discrimination marker (e.g., KLRG1 and the like)-positive iNKT cells can be determined by comparing the number of discrimination marker (e.g., KLRG1 and the like)-positive iNKT cells before administration of a CD1d-positive cell pulsed with an iNKT cell ligand and the number of discrimination marker (e.g., KLRG1 and the like)-positive iNKT cells after the administration. The expression levels are preferably compared based on the presence or absence of a significant difference.

After the administration of a CD1d-positive cell pulsed with an iNKT cell ligand means a time point when a sufficient period for the induction of memory iNKT cells has elapsed after administration of the CD1d-positive cell. Generally, the number of discrimination marker (e.g., KLRG1 and the like)-positive iNKT cells is measured again on or after day 5 in general, preferably after day 14, after administration of a CD1d-positive cell pulsed with an iNKT cell ligand. Since induced memory iNKT cells can survive for a long time, theoretically, there is no upper limit of the period from the administration of the CD1d-positive cells to the remeasurement of the number of the discrimination marker (e.g., KLRG1 and the like)-positive iNKT cells. However, a lapse of too long time may make the causal relationship with the administration of a CD1d-positive cell pulsed with an iNKT cell ligand indefinite. Generally, therefore, the number of discrimination marker (e.g., KLRG1 and the like)-positive iNKT cells is measured within 3 months, preferably 1 month.

Then, changes in the number of discrimination marker (e.g., KLRG1 and the like)-positive iNKT cells determined in step (1) and responsiveness of patient to an iNKT cell activation therapy are correlated.

In patients showing a good response to an iNKT cell activation therapy with CD1d-positive cell pulsed with an iNKT cell ligand, discrimination marker (e.g., KLRG1 and the like)-positive iNKT cells are induced and the number of the cells increases after administration of the CD1d-positive cells. The better the response is, the more the cell number increases. That is, the responsiveness of patient to an iNKT cell activation therapy with CD1d-positive cells pulsed with an iNKT cell ligand is predicted based on the positive correlation between an increase in the number of discrimination marker (e.g., KLRG1 and the like)-positive iNKT cells by the administration of CD1d-positive cells pulsed with an iNKT cell ligand, and responsiveness to the treatment method.

For example, when the number of the discrimination marker (e.g., KLRG1 and the like)-positive iNKT cells increases by the administration of CD1d-positive cell pulsed with an iNKT cell ligand, the target patient can be judged to show a good response to the iNKT cell activation therapy with CD1d-positive cell pulsed with an iNKT cell ligand and the treatment is highly possibly effective. Conversely, when the number of discrimination marker (e.g., KLRG1 and the like)-positive iNKT cells does not increase by the administration of CD1d-positive cells pulsed with an iNKT cell ligand, the target patient can be judged to show a weak response to the iNKT cell activation therapy with CD1d-positive cell pulsed with an iNKT cell ligand and the treatment is highly possibly ineffective.

By further administering a therapeutically effective amount of CD1d-positive cell pulsed with an iNKT cell ligand to patients judged to show a good response to the iNKT cell activation therapy with CD1d-positive cell pulsed with an iNKT cell ligand and for whom the treatment will be highly possibly effective, diseases of the patients can be treated. The present invention also provides such treatment method of a disease by CD1d-positive cell pulsed with an iNKT cell ligand. When CD1d-positive cell pulsed with an iNKT cell ligand is further administered to patients judged to show a satisfactory response to the iNKT cell activation therapy, memory iNKT cells are further induced in the patients, the therapeutic effect is enhanced by cytokines such as IFN-γ and the like produced from the memory iNKT cells and direct cytotoxic activity of the memory iNKT cells, and the disease can be treated.

Furthermore, the present invention also provides an isolation method of memory iNKT cells (isolation method of the present invention), which comprises isolating a discrimination marker (e.g., KLRG1 and the like)-positive and iNKT cell receptor-positive cell fraction from a lymphocyte-containing sample.

The sample is not particularly limited as long as it is a biological sample possibly containing a lymphocyte (preferably, memory iNKT cell). Preferably, peripheral blood, bone marrow, thymus, lymph node, lung, liver, tissue such as tumor tissue and the like, mononuclear cell fraction isolated therefrom and the like are used.

Isolation of a discrimination marker (e.g., KLRG1 and the like)-positive and iNKT cell receptor-positive cell can be preferably performed using an antibody that specifically recognizes a discrimination marker such as KLRG1 and the like and a soluble and pulsed with the iNKT cell ligand. A lymphocyte-containing sample is incubated with an antibody that specifically recognizes a discrimination marker such as KLRG1 and the like and a soluble CD1d pulsed with the iNKT cell ligand, and discrimination marker (e.g., KLRG1 and the like)-positive and iNKT cell receptor-positive cells are isolated by a cell sorter, panning, an antibody magnetic beads method and the like, whereby isolated memory iNKT cells can be obtained.

The "isolation" means that an operation to remove factors other than the target cells and components has been performed, and a naturally occurring state is no longer present. The purity of the "isolated memory invariant NKT cells" (percentage of memory iNKT cells in the total cell number) is generally not less than 70%, preferably not less than 80%, more preferably not less than 90%, still more preferably not less than 99%, most preferably 100%.

Memory iNKT cells can be used for an iNKT cell activation therapy including administering iNKT cells, by growing the isolated memory iNKT cells ex vivo and then returning them into the body. Since memory iNKT cells have high IFN-γ production ability and direct anti-tumor activity, a high anti-tumor effect can be expected.

Furthermore, the present invention provides a reagent containing the aforementioned antibody that specifically recognizes a discrimination marker such as KLRG1 and the like or a nucleic acid primer or nucleic acid probe that specifically detects mRNA or cDNA of a discrimination marker such as KLRG1 and the like. Using the reagent of the present invention, the above-mentioned detection method, prediction method, and isolation method of the present invention can be conveniently performed. Therefore, the reagent of the present invention is useful as a reagent for memory iNKT cell detection, a diagnostic reagent for predicting responsiveness of patient to an iNKT cell activation therapy, or a reagent for memory iNKT cell isolation.

The reagent of the present invention preferably further contains the aforementioned soluble CD1d pulsed with an iNKT cell ligand. That is, in a preferable embodiment, the reagent of the present invention contains an antibody that specifically recognizes a discrimination marker such as KLRG1 and the like or a nucleic acid primer or nucleic acid probe that specifically detects mRNA or cDNA of a discrimination marker such as KLRG1 and the like; and a soluble CD1d pulsed with the iNKT cell ligand in combination. In this embodiment, when an antibody that specifically recognizes a discrimination marker such as KLRG1 and the like and a soluble CD1d pulsed with the iNKT cell ligand are combined, each is preferably labeled with a fluorescent dye having a different fluorescence wavelength.

The reagent of the present invention may contain, in addition to an antibody that specifically recognizes a discrimination marker such as KLRG1 and the like or a nucleic acid primer or nucleic acid probe that specifically detects mRNA or cDNA of a discrimination marker such as KLRG1 and the like; and a soluble CD1d pulsed with the iNKT cell ligand, other antibody and reagent that may be used when the above-mentioned detection method, prediction method, and isolation method of the present invention are performed. These antibodies or reagents and the like may be combined in advance with the above-mentioned antibody, or nucleic acid primer or nucleic acid probe, or they may be stored in separate containers. As the antibody or reagent and the like, secondary antibody, substrate, labeling substance (e.g., fluorescent dye, enzyme), solid phase, reaction container, as well as treatment liquid and buffer for diluting antibody, manufacturer's instructions describing protocol and the like can be mentioned.

Respective components to be contained in the reagent of the present invention may be mixed in advance where necessary, or respective components may be placed in separate containers, packaged together and provided as a kit.

The contents disclosed in any publication cited in the present specification, including patents and patent applications, are hereby incorporated in their entireties by reference, to the extent that they have been disclosed herein.

The present invention is explained in more detail by the following Examples. However, the Examples are mere exemplifications of the present invention and do not limit the scope of the present invention in any manner.

EXAMPLES

[Materials and Methods]
Reagents

The following monoclonal antibodies (mAbs) were purchased from BD Biosciences, e-Bioscience, R&D Systems or Biolegend: anti-mouse CD1d (1B1), -CD3 (145-2C11), -CD4 (GK1.5), -CD11c (HL3), -CD19 (6D5), -CD25 (PC61), -CD27(LG.3A10), -CD28(37.51), CD43(S7), -CD44 (IM7), -CD62L (MEL-14), -CD69(H1.2F3), -CD107a (1D4B), -CD122 (TM-b1), -CD127 (A7R34), -IL15Ra, -Ly49H (3D10), -NK1.1 (PK136), -Ly49D(4E5), -NKG2D(CX5), -Ly6C(AL-21), -Klrg1(2F1), -PD1 (29F-1A12), -IFN-γ (XMG1.2), -T-bet(eBio4B10), -Eomes (Danllmag), CD1d-dimerix, TCR Vb screening panel were purchased from BD. For analysis, a FACS Calibur™ or Canto II instrument and CELLQuest™, Diva (BD Biosciences), or FlowJo (Tree Star) software were used. α-GalCer was synthesized and provided by Dr. Y. Ishii at RIKEN. iGB3 was purchased from Alexis Biochemicals. GSL of *Sphingobium yanoikuyae* was purified by Kawahara as previously described (Kawahata et al., 2006. Microbiol Immunol 50, 67-71).

Mice and Cell Lines

Pathogen-free, 6-8 week old C57BL/6 mice were purchased from CLEA Japan. B6 mice, Jα18$^{-/-}$ mice and iNKT-cloned mice were maintained under specific pathogen-free conditions and treated in compliance with institutional guidelines. B16 melanoma and NIH3T3 cell lines were purchased from the American Type Culture Collection. B16 (CD1d-B16), NIH3T3 (CD1d-NIH3T3) and HEK293 (CD1d-293) cells expressing high levels of CD1d were generated by retrovirus transduction.

Cell Preparation

Bone marrow-derived DCs were generated in the presence of GM-CSF and pulsed with 100 ng/ml α-GalCer for 48 h at day 6 and matured by LPS. In some experiments, other NKT ligands, 10 µg/ml iGB3 or GSL were used for pulsing instead of α-GalCer. Mononuclear cells (MNCs) from spleen, lung, and liver were isolated. In brief, splenocytes were obtained by pressing the spleen through a 70 µm cell strainer and erythrocytes were lysed with ACK lysing buffer (GIBCO) followed by two washes in RPMI. For isolation of lung and liver MNCs, the tissues were digested with collagenase D (Roche) and then layered on percoll gradients (40/60%) (Amersham Pharmacia Biotec) and centrifuged for 20 min at 900 g.

Elispot Assay

ELISPOT assays for IFN-γ secreting cells were performed by culturing with or without 100 ng/ml α-GalCer for 16 h. The number of ligand-dependent IFN-γ spots was counted microscopically.

Cytokine Secretion Assays and Intracellular Staining

IFN-γ release from iNKT cells was determined using a cytokine secretion detection kit according to the manufacturer's instructions (Miltenyi Biotec Inc.). Briefly, cells were incubated on ice for 5 min with IFN-γ-capture reagent and then diluted with warm RPMI with 5% FCS following incubation for 45 min at 37° C. After two washes, cells were resuspended in cold MACS buffer and incubated with PE-coupled IFN-γ-detection reagent for 10 min at 4° C., followed by staining of other cell surface markers. For intracellular cytokine staining of iNKT cells for analysis by flow cytometry, isolated lung MNCs were stimulated with 10 µg/ml immobilized anti-CD3 Ab and 2 µg/ml soluble anti-CD28 Ab in the presence of Golgi Plug (BD Bioscience) for 2 h and then preincubated with anti-CD16/32 Ab to block non-specific binding of antibodies to FcγR, washed, incubated with monoclonal antibodies to the indicated cell surface markers. The cells were then permeabilized in Cytofix-Cytoperm Plus (BD Bioscience) and stained with anti-IFN-γ, mAbs.

Cytotoxicity Assay

The cytotoxic activity of lung MNCs against B16 melanoma cells was analyzed using LDH assay kit according to the manufacturer's instructions (Takara Bio Company). In brief, $1\times10^4$ B16 melanoma cells were cultured with pooled lung MNCs from naïve or DC/Gal immunized mice at various effector/target (E/T) ratios for 16 h. The culture supernatant was incubated with freshly prepared Reaction Mixture containing the tetrazolium salt and absorbance was measured at 490 nm. Data are mean±s.d. of triplicate wells from three independent experiments. After subtracting the background control value, cytotoxicity values (%) were calculated as follows.

$$\text{Cytotoxicity (\%)} = \{(\text{Effector:Target cell mix-effector cell control}) - \text{spontaneous target cell control}\} / (\text{Maximum target control-spontaneous target cell control}) \times 100$$

Microarray

Total RNA extracted from samples of isolated iNKT cells was used for microarray analysis with a GeneChip Mouse Genome 430 2.0 Array; all procedures were performed according to the manufacturer's instructions (Affymetrix). Data were analyzed by using GeneSpring software (Agilent Technologies).

TCR Vβ Repertoire Assay

Each iNKT cell subset was isolated to high purity. Total RNA was extracted and reverse transcribed to synthesize first-strand cDNA using a SMARTer RCAE cDNA amplification kit (Clontech). Both universal mix primer and primers specific for the TCR constant region sequence were used for second-strand amplifications, resulting in TCRβ PCR products of high purity, which were then submitted for highthroughput DNA sequencing of long reads using a Roche 454-GS Junior system. All reads of TCRβ repertoire sequence were analyzed using Perl scripts based on the USEARCH algorithm (http://drive5.com/usearch/). V-region consensus sequences in each cluster were searched on the IMGT sites (http://www.imgt.org/IMGTvquest/share/textes/).

In Vivo Tumor Experiments

Mice were immunized with or without $1 \times 10^6$ DC/G. Four months later, the mice were injected with $2 \times 10^5$ B16 melanoma cells intravenously. 14 days later, mice were sacrificed and the numbers of lung metastases were analyzed. In some experiments, mice were treated with 300 μg/mouse anti-NK1.1 Ab twice per week from 2 days before inoculation of B16 cells.

Quantitative PCR Assay

To evaluate gene expression by iNKT cells, FACS-sorted iNKT cells were directly subjected to cDNA synthesis and pre-amplification, without purifying RNA, using a CellsDirect One-Step qRT-PCR Kit (Invitrogen) with a mixture of pooled genespecific primers (0.2 μM each). After 18 cycles of pre-amplification (each cycle: 95° C. for 30 seconds, 60° C. for 4 minutes), an aliquot was used for quantitative PCR using FastStart Universal Probe Master (Roche), a gene-specific forward and reverse primer, and the corresponding FAM-labeled hydrolysis probe (Universal Probe Library Set, Roche). Quantitative PCR was performed on ABI PRISM 7000 (Applied Biosystems). Gene expression was measured by $\Delta \Delta C_T$ method in which HPRT1 expression was used as the internal control.

Luminex and ELISA $1 \times 10^5$ sorted KLRG1$^+$ or KLRG1$^-$ iNKT cells were stimulated with 10 μg/ml immobilized CD3 Ab plus 10 μg/ml soluble CD28 Ab for 24 h. The culture supernatants were analyzed for IFN-γ production by ELISA (BD) and CCL3 and CCL4 production by Luminex (Bio-Rad).

Pulse-Chase Experiments

To assess the turnover of iNKT cells in vivo, 1 μg of BrdU was administered intraperitoneally to mice just before immunization with DC/Gal; then for 7 days, drinking water that contained 0.8 mg/ml of BrdU was given ad libitum. The iNKT cells were labeled with the appropriate mAb, and then labeling with BrdU was assessed with a BrdU Flow Kit (Becton Dickinson) on fixed cells. For the latter, cells were fixed in 100 μl of Cytofix-Cytoperm buffer for 20 min on ice, washed with perm-wash buffer and incubated on ice in 100 μl of Cytoperm Plus Buffer for 10 min. They were then refixed with Cytofix-Cytoperm buffer on ice for 5 min, treated with 300 μg/ml of DNase for 1 h at 37° C. and then stained with anti-BrdU for 20 min at room temperature for flow cytometric analysis.

Statistical Analysis.

Differences were analyzed using Mann-Whitney U-test. P<0.05 was considered statistically significant.

[Results]

Example 1: Long-Term Persistence of KLRG1$^+$iNKT Cells in Lung

The present inventors have previously reported that DC/Gal induced an expanded population of IFN-γ producing iNKT cells for 2-4 days in the mouse spleen, but that cell numbers returned to basal levels a week later (Fujii et al., 2002. Nature Immunology 3, 867). In the current study, the present inventors found that in the lung of wild type or tumor-bearing mice the increased number of IFN-γ-producing iNKT cells persisted for long periods after treatment with DC/Gal (FIG. 1a-c). Also, lung mononuclear cells (MNCs) in these immunized mice displayed anti-tumor activity against tumor cells (FIG. 1d).

CD4$^-$ iNKT cells in the steady state have been reported to be an antitumor iNKT cell subset (Crowe, N. Y. et al., 2005. J. Exp. Med. 202, 1279). However, they could not detect any differences in the ratio or IFN-γ producing capacity of CD4$^-$ or CD4$^+$ subsets of iNKT cells in the lungs of DC/Gal-injected mice in comparison with naïve iNKT cells. The CD4 marker on iNKT cells was not useful as a simple marker of long-lived antitumor iNKT cells. Therefore, to search for a specific marker of these effective iNKT cells, the iNKT cells of mice immunized with DC/Gal a month previously were analyzed by gene array (FIG. 1e). As a result, KLRG1 expression was detected specifically in iNKT cells from DC/Gal-treated mice.

Example 2: Identification of iNKT Cell Memory Phase

The present inventors detected an expansion of KLRG1$^+$ iNKT cells after injection of dendritic cells, CD1d-transfected NIH3T3 cells, dendritic cells loaded with α-GalCer (DC/Gal), CD1d-transfected B16 melanoma cells loaded with α-GalCer (CD1d-B16/Gal) or NIH3T3 cells loaded with α-GalCer (CD1d-NIH3T3/Gal) into C57BL/6 mice. The present inventors could not detect KLRG1$^+$iNKT cells in uninfected naïve mice or in mice given DC or CD1d-transfected NIH3T3 cells while verified the expansion of KLRG1$^+$iNKT cells in mice injected with DC/Gal, CD1d-B16/Gal, or CD1d-NIH3T3/Gal (FIG. 2a).

Flow cytometric analysis of the expression of surface molecules (other than KLRG1) expressed in KLRG1$^+$ iNKT cells indicated that the cells expressed more CD43, CD49d, Ly6C and NKG2D, and less CD69, CD127 and CD27 than the naïve cells (FIG. 2b). With regard to the analysis of CD4 expression, the KLRG1$^+$ iNKT subset contains an equal frequency of CD4$^+$ and CD4$^-$ cells, although naïve iNKT cells have more CD4+ cells. The KLRG1$^+$ iNKT cells did not express NK cell activation/memory markers such as LPAM-1, Ly49D and Ly49H. To investigate the kinetics of proliferation of iNKT cells, the frequency of KLRG1$^+$iNKT cells was then analyzed from day 2 to 12 weeks after immunization with DC/Gal. The result indicated that the expansion began 2 days after DC/Gal administration (FIG. 2c). The absolute number of total iNKT cells expanded robustly and then declined to the steady state level (FIG. 2d). Interestingly, the KLRG1$^+$ iNKT cells expanded and then declined until day 30 after DC/Gal administration, but after the contraction phase, continued to be maintained in the lung and liver, but not spleen (FIG. 2e).

Example 3: Characterization of KLRG1+ iNKT Cells

The KLRG1$^+$ iNKT cells that had been maintained long term after immunization with DC/Gal were assessed by carrying out the quantitative real time PCR of cytokine, chemokine and cytotoxic molecules. The KLRG1$^+$ iNKT cells were found to express cc13, cc14 and granzyme A and had higher levels of IFN-γ, and fasL transcripts than naïve or KLRG1$^-$ iNKT cells (FIG. 3a). Then, the present inventors verified at the protein level that the KLRG1$^+$iNKT cells from DC/Gal-injected mice expressed high levels of granzyme A, but that iNKT cells of naïve mice did not (FIG. 3b). Degranulation of KLRG1$^+$ iNKT cells was also enhanced, as assessed by LAMP-1 (CD107a) expression after in vitro stimulation with anti-CD3 plus anti-CD28 mAbs.

When IFN-γ production in iNKT cells from DC/Gal-injected or naïve mice was assessed 2 h after stimulation, the IFN-γ MFI of KLRG1$^+$ iNKT cells was much higher than that of naïve iNKT cells (FIG. 3c). Also, the amounts of IFN-γ, CCL3 and CCL4 produced by KLRG1$^+$ iNKT cells were higher (FIG. 3d) when compared. On the other hand, the KLRG1$^+$ iNKT cells produced no IL-4, IL-10 or IL-17.

From the above, KLRG1$^+$ iNKT cells were shown to have a lower threshold for activation than that of naïve iNKT cells and produce cytokine species distinct from those produced by steady-state iNKT cells, indicating their discrete function as memory iNKT cells.

Next, as a result of the analysis of transcription factors, the present inventors found that the expression of eomes, tbx21 and runx3 by KLRG1$^+$ iNKT cells was higher than in naïve iNKT cells (FIG. 3e). On the other hand, the expression of GATA3 and RORγ by KLRG1$^+$ iNKT cells was lower than in naïve cells (FIG. 3e). To study the effect of IFN-γ-production by KLRG1$^+$ iNKT cells, the DC/Gal treated mice were challenged with the B 16 melanoma i.v. 4 months later to examine the metastasis of tumor cells. The present inventors first verified the increased frequency of IFN-γ-producing KLRG1$^+$ iNKT cells in vivo (FIG. 3f), and two weeks after B16 melanoma challenge, they counted the number of tumor metastases in the lung as a measure of long-lived resistance. Metastases were suppressed in mice given DC/Gal, but observed in anti-NK1.1 antibody-treated mice (FIG. 3g). This result showed a prominent anti-tumor effect by KLRG1$^+$ iNKT cells.

Example 4: The iNKT-Cell Recall Response

To test whether iNKT cells survived longer in a memory state in DC/Gal-injected mice, the inventors performed a pulse and chase study. The KLRG1$^+$iNKT cells incorporated BrdU for 7 days after DC/Gal treatment and the cells one month after administration were still BrdU$^+$, suggesting that the KLRG1$^+$iNKT cells were maintained (FIG. 4a).

In order to directly demonstrate that memory iNKT cell survival, the present inventors adoptively transferred KLRG1$^+$ iNKT cells into third party Jα18 KO mice, but in this case used iNKT cells from Vα1$^+$ iNKT cloned mice, which the present inventors had previously established as Vα14NT mice and permitted us to track the transferred cells as CD1d dimer$^+$venus$^+$ (see; Watarai, H. et al., 2010. Blood 115, 230-237). KLRG1$^+$ iNKT cells from DC/Gal-injected Vα14$^+$iNKT cloned mice showed similar features as those from DC/Gal-injected WT mice. The KLRG1$^+$ Vα14$^+$venus$^+$iNKT cells that had been transferred into Jα18−/− mice were expanded in a secondary response when they re-encountered DC/Gal (FIG. 4b). This result suggests that KLRG1$^+$ iNKT cells were capable of a recall antigen response. Next, to better reflect the physiological condition, small numbers of naïve Vα14$^+$venus$^+$iNKT cells (i.e., KLRG1$^-$ iNKT cells) were transferred into C57BL/6 mice. Adoptive transfer of naïve Vα14$^+$ iNKT cells from Vα14$^+$ iNKT cloned mice into C57BL/6 mice allowed us to distinguish between antigen-experienced iNKT cells and iNKT cells newly developed from the thymus. The Vα14$^+$venus$^+$ iNKT cells were rarely detected in C57BL/6 mice that had been transferred with naïve Vα14$^+$venus$^+$iNKT cells 3 months before, but KLRG1$^+$ Vα14$^+$venus$^+$iNKT cells were detectable 3 months later in mice that had been transferred and subsequently immunized with DC/Gal (FIG. 4c). The proliferated Vα14$^+$venus$^+$iNKT cells were found to continue the expression of KLRG1 (FIG. 4d).

The above results suggested that memory iNKT cells can be long-lived in the periphery and participate in a recall antigen response, similar to memory NK cells.

Next, the present inventors verified that an antigen-specific secondary response could occur in DC/Gal-immunized WT mice without adoptive transfer of iNKT cells. The memory iNKT cells expanded more than in a primary response when boosted with DC/Gal 2 months later, an activity similar to that seen with memory NK cells. The KLRG1$^+$ iNKT cells boosted by DC pulsed with low dose (10 ng/ml) of α-GalCer expanded robustly, 5 times more than following the primary response to DC pulsed with low dose α-GalCer, but they were not expanded by DC alone, i.e., without antigen (FIG. 5a). It is thought that iNKT cells can respond to various exogenous and endogenous ligands. Interestingly, when DC/Gal-immunized mice were boosted with DC/iGB3 or DC/GSL, we detected expansion of the KLRG1$^+$ iNKT cells in the lung (FIG. 5a) and liver, but this was almost to the same level as seen in the primary responses.

Therefore, KLRG1$^+$iNKT cells can specifically recognize and respond to cognate antigen. In other words, like memory T cells, memory iNKT cells are self-renewing, long-lived, and can mount a secondary response, with expansion greater than 10-70 fold in the lung and liver.

Example 5: Analysis of TCR Repertoire of Memory iNKT Cells

It is well-known that the α chain of the iNKT cell TCR is invariant; however, there is more variability in the β chain, although it is restricted mainly to Vβ7, Vβ8 and Vβ2. The inventors next used flow cytometry to evaluate the TCRVβ repertoire of iNKT cells in naïve mice, α-GalCer-loaded DC-injected mice and DC/Gal-boosted mice, in order to look for evidence of antigen-selection of the memory cells (FIG. 5b). They did not find any accumulation of a specific Vβ repertoire in DC/Gal-injected or DC/Gal-injected and DC/Gal-boosted mice compared to naïve iNKT cells. On the other hand, there was an increase in TCRVβ8.1$^+$/8.2$^+$ iNKT cells, accompanied by a decrease of other TCRVβ$^+$iNKT cells in DC/GSL or DC/Gal-DC/GSL boosted mice, whereas TCRVβ7$^+$ iNKT cells increased in DC/iGB3-injected or DC/Gal-DC/iGB3 boosted mice (FIG. 5b).

Next, the inventors used massively parallel RNA sequencing from a group of pooled iNKT cells to analyze the Vβ complementary-determining regions (CDR1β, CDR2β and CDR3β). In initial sequence analysis, the inventors found that the predominant pattern of TCR Vβ usage by iNKT cells in naïve, DC/Gal-administered and DC/Gal-boosted mice, i.e., Vβ2, Vβ7 and Vβ8 genes, was similar to that observed by FACS analysis (FIG. 5b). When the inventors further analyzed the RNA sequences in detail after clustering of CDR1 and CDR2, the inventors found that the CDR1β and CDR2β of the KLRG1[+] iNKT cells almost completely matched those of naïve iNKT cells.

There is another possible mechanism to form a memory iNKT cell repertoire. Unlike their TCRα chain, both the CDR3 composition of the Vβ chains and association with different Jρ segments, and so therefore the junctional diversity of CDR3β, are quite heterogeneous in naïve mice. Therefore, the present inventors hypothesized that the TCR Vβ repertoire would become more focused in the iNKT cells in the effector or memory phases, i.e., the pattern of CDR3 regions would be clonal in some cases. Even after clustering the common CDR1 and CDR2, the CDR3βs of memory iNKT cells were still heterogeneous, however, the CDR3β sequences were different from those of naïve iNKT cells (FIG. 5c). In addition, such clones accumulated in clusters and became more prominent after boosting (FIG. 5c). Interestingly, further analysis for the clusters of CDR3 reads revealed that naïve iNKT cells were comprised of many different small read clusters, i.e., very few of large read clusters, while activated iNKT, memory iNKT 12 cells and boosted memory iNKT cells were selected to make specific large clusters in all the Vβ families (FIG. 5d).

To further compare iNKT cells with memory T cells, the present inventors performed principal component analysis of whole CDR3 clusters to identify those with specific features of memory iNKT and/or typical memory T cells and successfully identified such CDR3 clusters (FIG. 5e(i)): The group (1) contains CDR3 clusters where any reads in CDR3β could be detected in the effector and the boosting phase (FIG. 5e(ii)); the group (2) was composed of CDR3 clusters whether any reads in CDR3β could be detected in effector but more in the memory and the boosting phase (FIG. 5e(iii)). The inventors detected TCR clone reads in the groups (1) and (2) were enriched in Vβ8.2 and Vβ8.3 and in Vβ7 and Vβ8.3, respectively. These results indicate that the iNKT cells may be negatively selected by activation-induced cell death, whereas some of them survive with memory function in a CDR3β-dependent manner.

INDUSTRIAL APPLICABILITY

According to the present invention, memory iNKT cells can be easily detected and isolated using an antibody to KLRG1. The present invention enables easy evaluation of the responsiveness of the patient to an iNKT cell activation therapy.

This application is based on a patent application No. 2014-152394 filed in Japan (filing date: Jul. 25, 2014), the contents of which are incorporated in full herein.

The invention claimed is:

1. A method of isolating a memory invariant NKT cell, comprising:
    contacting a lymphocyte-containing sample with an antibody that specifically recognizes Killer Cell Lectin-like Receptor Subfamily G, Member 1 (KLRG1), and
    isolating a KLRG1-positive and invariant NKT cell receptor-positive cell fraction from the lymphocyte-containing sample.

2. The method according to claim 1, wherein the the lymphocyte-containing sample is further contacted with a soluble CD1d pulsed with an invariant NKT cell ligand.

3. The method of claim 2, wherein the antibody specifically recognizes the KLRG1 extracellular domain.

4. The method of claim 3, wherein the invariant NKT cell ligand is selected from the group consisting of α-glycosylceramide, isoglobotrihexosylceramide (iGB3), (2S,3S,4R)-1-O-(α-D-galactopyranosyl)-N-tetracosanoyl-2-amino-1,3, 4-nonanetriol (OCH), and glycosphingolipid (GSL).

5. The method of claim 4, wherein the invariant NKT cell ligand is α-galactosylceramide (α-GalCer).

6. The method of claim 4, wherein the invariant NKT cell ligand is glycosphingolipid (GSL) of *Sphingobium yanoikuyae*.

7. The method of claim 2, wherein the invariant NKT cell ligand is selected from the group consisting of α-glycosylceramide, isoglobotrihexosylceramide (iGB3), (2S,3S,4R)-1-O-(α-D-galactopyranosyl)-N-tetracosanoyl-2-amino-1,3, 4-nonanetriol (OCH), and glycosphingolipid (GSL).

8. The method of claim 7, wherein the invariant NKT cell ligand is α-galactosylceramide (α-GalCer).

9. The method of claim 7, wherein the invariant NKT cell ligand is glycosphingolipid (GSL) of *Sphingobium yanoikuyae*.

10. The method of claim 1, wherein the antibody specifically recognizes the KLRG1 extracellular domain.

* * * * *